(12) United States Patent
Choi et al.

(10) Patent No.: US 10,321,886 B2
(45) Date of Patent: Jun. 18, 2019

(54) WORKSTATION, MEDICAL IMAGING APPARATUS HAVING THE SAME AND METHOD FOR CONTROLLING THEREOF

(71) Applicant: Samsung Electronics Co., Ltd., Gyeonggi-do (KR)

(72) Inventors: Ji Young Choi, Suwon-si (KR); Jong Beom Ra, Daejeon (KR); Seok Hwan Jang, Seoul (KR); Seung Eon Kim, Bucheon-si (KR); Duhgoon Lee, Yongin-si (KR)

(73) Assignees: Samsung Electronics Co., Ltd., Suwon-si (KR); Korea Advanced Institute of Science and Technology, Daejeon (KR)

( * ) Notice: Subject to any disclaimer, the term of this patent is extended or adjusted under 35 U.S.C. 154(b) by 70 days.

(21) Appl. No.: 15/415,535

(22) Filed: Jan. 25, 2017

(65) Prior Publication Data
US 2017/0209111 A1    Jul. 27, 2017

(30) Foreign Application Priority Data

Jan. 25, 2016  (KR) .................. 10-2016-0008855
Nov. 9, 2016   (KR) .................. 10-2016-0148978

(51) Int. Cl.
| | |
|---|---|
| G06K 9/00 | (2006.01) |
| A61B 6/00 | (2006.01) |
| G06T 11/00 | (2006.01) |
| A61B 6/02 | (2006.01) |
| A61B 6/03 | (2006.01) |
| A61B 6/04 | (2006.01) |

(52) U.S. Cl.
CPC ............ *A61B 6/5264* (2013.01); *A61B 6/027* (2013.01); *A61B 6/032* (2013.01); *A61B 6/4078* (2013.01); *A61B 6/4085* (2013.01); *A61B 6/501* (2013.01); *A61B 6/5205* (2013.01); *G06T 11/003* (2013.01); *G06T 11/005* (2013.01); *A61B 6/0457* (2013.01); *A61B 6/488* (2013.01)

(58) Field of Classification Search
CPC ......... A61B 5/055; A61B 6/032; A61B 6/037; A61B 6/5264; G06T 7/0012
USPC ........ 382/132, 131, 254, 25, 128; 378/4, 19, 378/20; 600/484
See application file for complete search history.

(56) References Cited

U.S. PATENT DOCUMENTS

| | | | |
|---|---|---|---|
| 6,341,179 B1 * | 1/2002 | Stoyle | G06T 11/008 382/254 |
| 8,170,312 B2 * | 5/2012 | Chen | G06T 7/0016 382/128 |
| 9,826,942 B2 * | 11/2017 | Sebok | A61B 6/032 |

(Continued)

*Primary Examiner* — Charlotte M Baker

(57) ABSTRACT

Disclosed herein are workstation, medical imaging apparatus having the same and method for controlling thereof. The medical imaging apparatus includes an X-ray source configured to irradiate X-rays; an X-ray detector configured to obtain raw data by detecting X-rays irradiated from the X-ray source; and an image processor configured to determine a motion parameter to represent motion of at least one of an object, the X-ray source, and the X-ray detector from a medical image reconstructed based on the obtained raw data, and reconstruct a motion-compensated medical image of the object based on a virtual trajectory of the X-ray source generated based on the determined motion parameter.

19 Claims, 24 Drawing Sheets

(56) References Cited

U.S. PATENT DOCUMENTS

2009/0086888 A1* 4/2009 Hagiwara ................ A61B 6/04
378/20
2016/0335764 A1* 11/2016 Kawagishi ............ G06T 7/0012

* cited by examiner

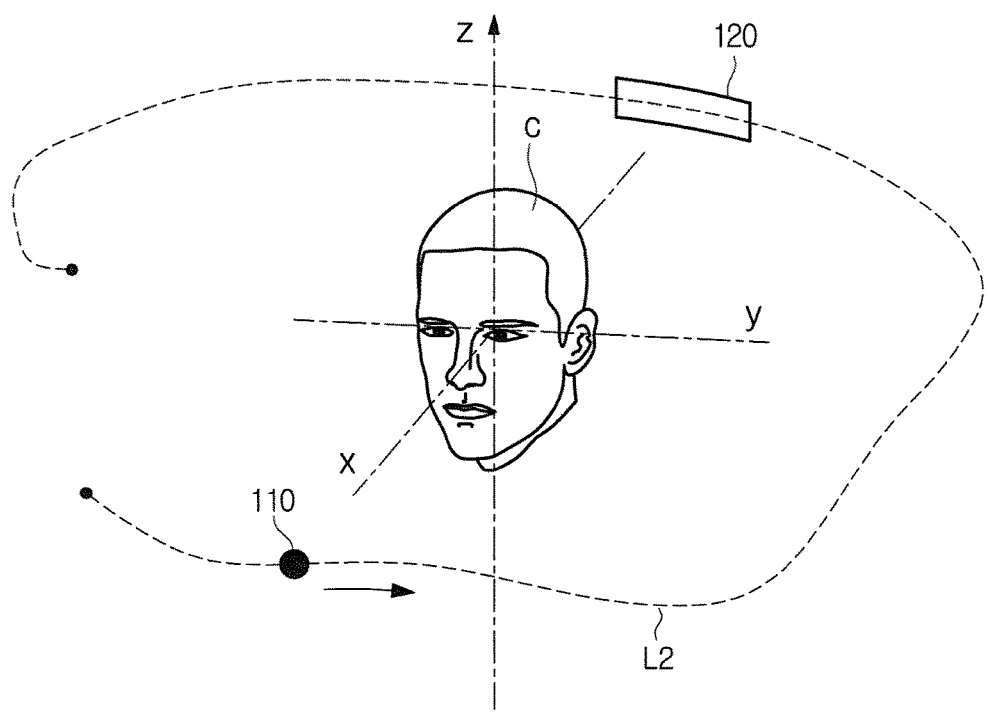

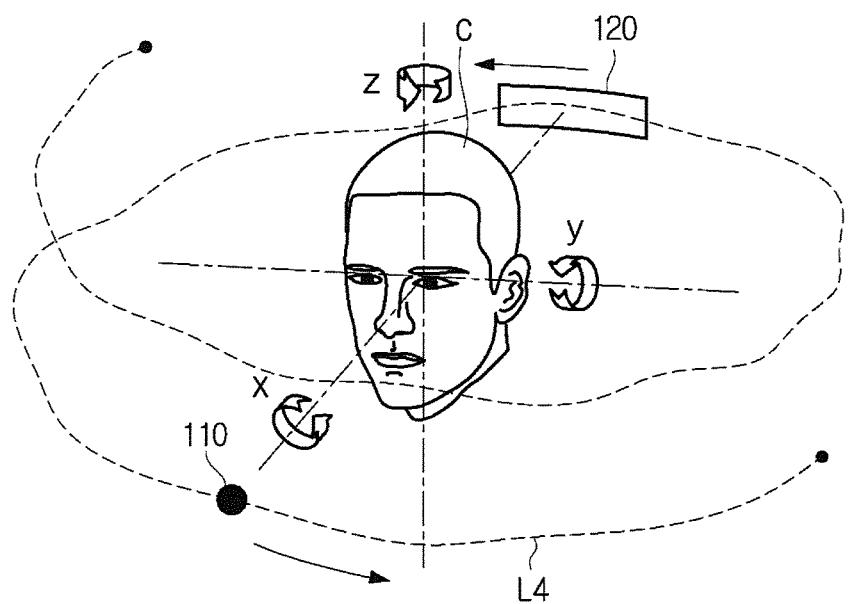

WORKSTATION, MEDICAL IMAGING APPARATUS HAVING THE SAME AND METHOD FOR CONTROLLING THEREOF

CROSS-REFERENCE TO RELATED APPLICATION(S) AND CLAIM OF PRIORITY

The present application is related to and claims the benefit of Korean Patent Application No. 10-2016-0008855, filed on Jan. 25, 2016, and Korean Patent Application No. 10-2016-0148978, filed on Nov. 9, 2016, the disclosures of which are incorporated herein by reference in its entirety.

TECHNICAL FIELD

Embodiments of the present disclosure relate to a workstation, medical imaging apparatus having the workstation, and method for controlling the workstation.

BACKGROUND

Medical imaging apparatuses are generally used to obtain a medical image by imaging an internal part of an object, and use the obtained medical image in diagnosis. Specifically, the medical imaging apparatus scans and processes structural details, internal tissues, and fluid flows in the body, and displays the result to the user. The user, e.g., a doctor may diagnose a health condition and illness of a patient using the medical image output from the medical imaging apparatus. The higher the precision of the medical image is, the more accurately the user may examine a condition of the patient. Accordingly, there is research underway to find a method for obtaining more precise medical images.

SUMMARY

To address the above-discussed deficiencies, it is a primary object to provide a medical imaging apparatus includes an X-ray source configured to irradiate X-rays; an X-ray detector configured to obtain raw data by detecting X-rays irradiated from the X-ray source; and an image processor configured to determine a motion parameter to represent motion of at least one of an object, the X-ray source, and the X-ray detector from a medical image reconstructed based on the obtained raw data, and reconstruct a motion-compensated medical image of the object based on a virtual trajectory of the X-ray source generated based on the determined motion parameter.

Here, the image processor is configured to determine a motion parameter value at at least one scan point of time or scan time by applying an image quality metric process on the medical image reconstructed based on the obtained raw data.

Also, the image processor is configured to set at least one control point, determine a motion parameter value at the at least one control point, and form a graph for each motion parameter by approximation of the determined motion parameter value.

Also, the image processor is configured to set the motion parameter to be a variable, apply the image quality metric process in which at least one of an entropy vale, a sharpness value, and a gradient value is set to be a resultant value, and determine a motion parameter value at least one scan point of time or scan time.

Also, the image processor is configured to calculate a motion parameter value at each scan point of time or scan time using the graph, and generate a virtual trajectory of the X-ray source by reflecting motion of the object based on the calculated motion parameter value.

Also, the image processor is configured to perform a weighting process on projection data derived from the raw data based on a distance between the X-ray source and the X-ray detector on the virtual trajectory of the X-ray source.

Also, the image processor is configured to perform a filtering process on projection data derived from the raw data based on a tangential direction of the virtual trajectory of the X-ray source.

Also, the motion parameter comprises at least one of a motion of the object itself and a relative motion of the object reflecting a motion of at least one of the X-ray source and the X-ray detector.

Also, the motion parameter comprises a parameter to represent a distance between the X-ray source and the X-ray detector.

Also, the image processor is configured to identify a marker in a partial medical image obtained by irradiation of X-rays on the object with a marker attached thereon by comparing a pre-stored template partial medical image with the partial medical image.

Also, the image processor is configured to determine an initial motion parameter value by tracking a position of the marker identified in the partial medical image, and reconstruct a motion-compensated medical image of the object based on the determined initial motion parameter value.

In accordance with one aspect of the present disclosure, a workstation includes an interface configured to receive a command to scan an object from a user; a controller configured to control operation of an X-ray source and X-ray detector to obtain raw data under the received scan command; and an image processor configured to create a first medical image from the raw data, generate a virtual trajectory of the X-ray source based on a motion parameter determined from the first medical image, and reconstruct a motion-compensated second medical image of the object based on the virtual trajectory of the X-ray source.

Also, the image processor is configured to determine a motion parameter value at at least one scan point of time or scan time by applying an image quality metric process on the first medical image reconstructed based on the obtained raw data.

Here, the image processor is configured to perform a weighting process on projection data derived from the raw data based on a distance between the X-ray source and the X-ray detector on the virtual trajectory of the X-ray source.

Here, the image processor is configured to perform a weighting process on projection data derived from the raw data based on one of the determined motion parameters that represents a distance between the X-ray source and the X-ray detector.

In accordance with one aspect of the present disclosure, a method for controlling a workstation includes receiving a command to scan an object from a user; controlling operation of an X-ray source and X-ray detector to obtain raw data under the received command; and creating a first medical image from the raw data, generating a virtual trajectory of the X-ray source based on a motion parameter determined from the first medical image, and reconstructing a motion-compensated second medical image of the object based on the virtual trajectory of the X-ray source.

Here, reconstructing a motion-compensated second medical image comprises, determining a motion parameter value at least one scan point of time or scan time by applying an image quality metric process on the first medical image reconstructed based on the obtained raw data.

Also, reconstructing a motion-compensated second medical image comprises, setting at least one control point, determining a motion parameter value at the at least one control point, and forming a graph for each motion parameter by approximation of the determined motion parameter value.

Also, restoring a background region of the first frame image based on the comparison of the first frame image and the one or more second frame images comprises, calculating a motion parameter value at each scan point of time or scan time using the graph, and generating a virtual trajectory of the X-ray source by reflecting motion of the object based on the calculated motion parameter value.

As described above, it is possible to perform more accurate back projection by adjusting a back projection position based on the motion parameter.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 9A and 9B illustrate virtual trajectories of an X-ray source created by reflecting motions of an object, according to various embodiments of the present disclosure;

DETAILED DESCRIPTION

FIGS. 1A through 17, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device.

A medical imaging apparatus refers to a device for obtaining a medical image of an internal part of an object. The object may be, but not exclusively, a living body of a human or animal, an organ in the living body, such as blood vessels, bones, muscles, etc., or anything whose internal structure may be imaged by various types of signals irradiated from the medical imaging apparatus, such as phantom.

The medical imaging apparatus as will be described below includes all kinds of devices for obtaining medical images of internal parts of objects. For example, the medical imaging apparatus may include any device capable of obtaining medical images about internal parts of objects, such as a magnetic resonance imaging (MRI) device, an ultrasonic imaging device with an ultrasonic probe, etc. Furthermore, the medical imaging apparatus may include any tomographic scanners, such as a computed tomography (CT) imaging device, an optical coherence tomography (OCT), and a positron emission tomography (PET)-CT imaging device.

The CT imaging device will be described as an example of the medical imaging apparatus, but the following embodiments are not limited thereto but may include any device capable of obtaining medical images.

Figure 1A:
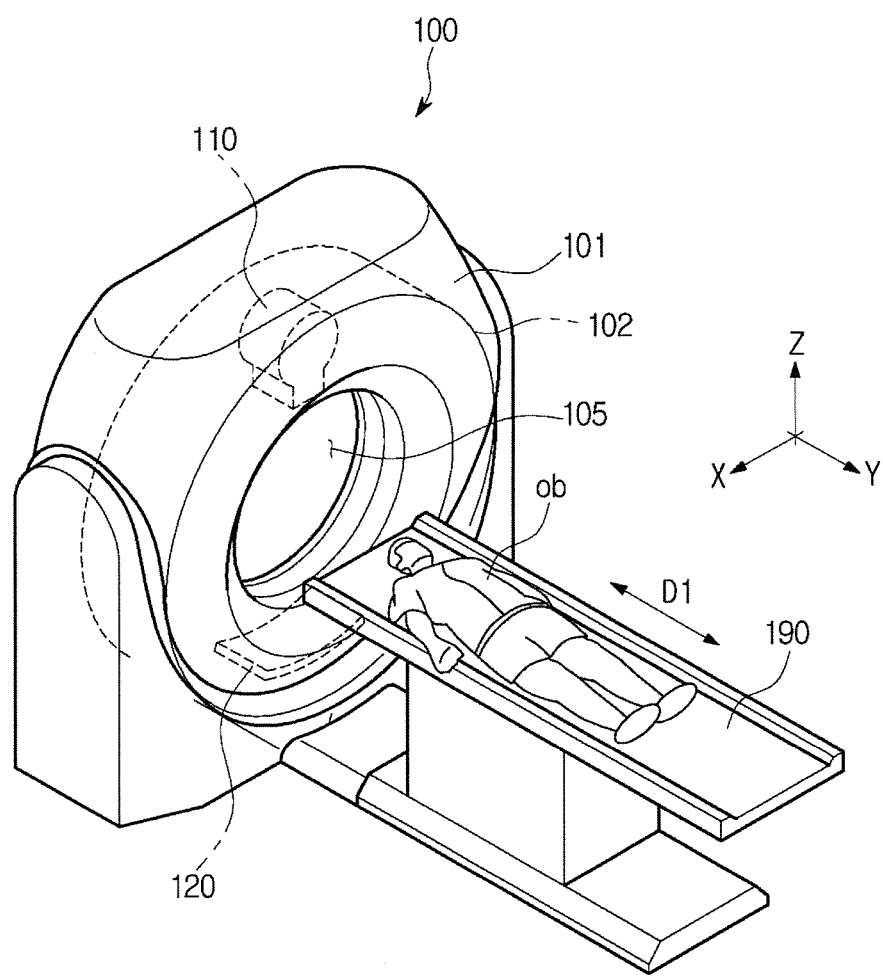
FIGS. 1A and 1B illustrate the exterior of an exemplary medical imaging apparatus according to various embodiments of the present disclosure.
Figure 1B:
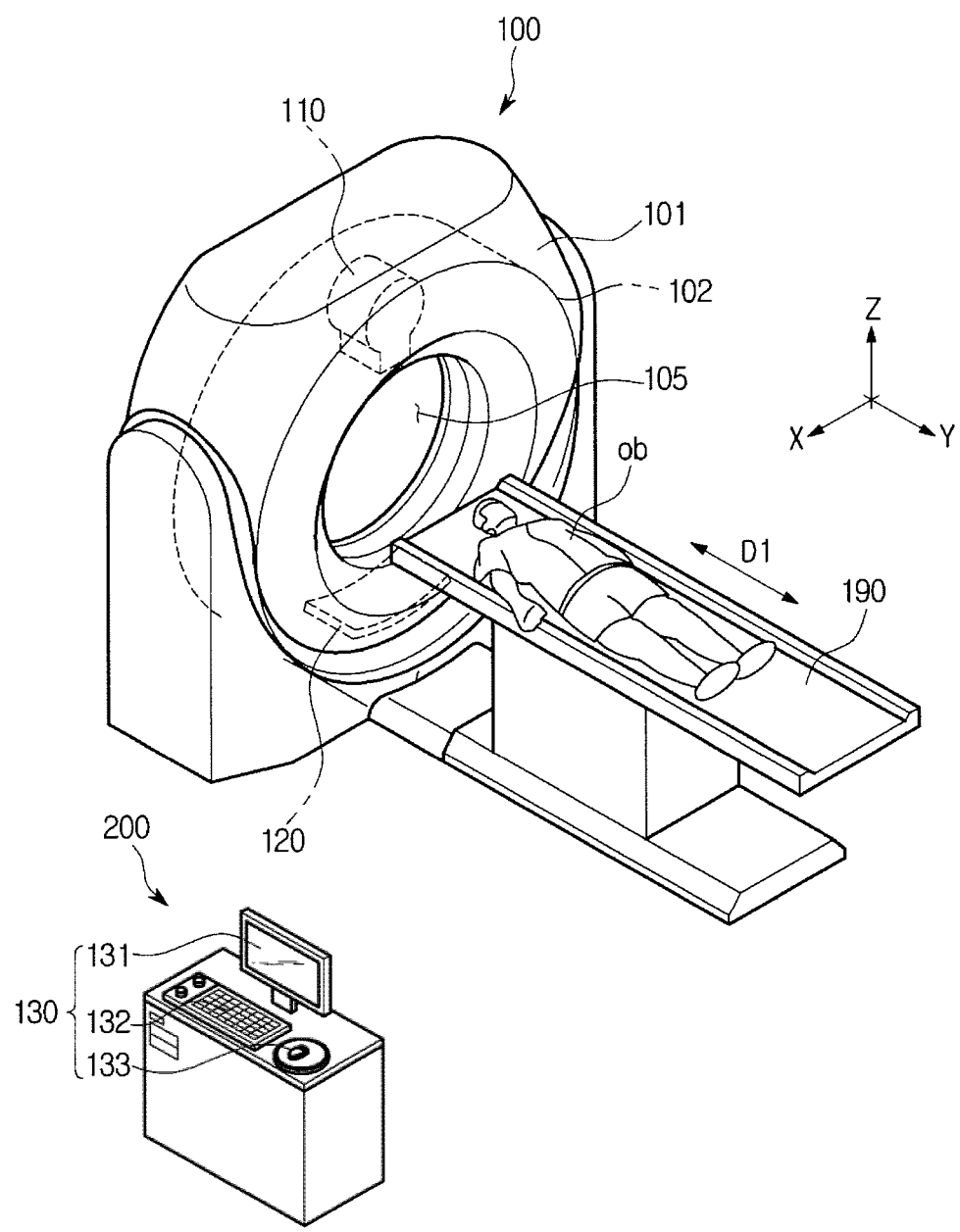
Figure 2:
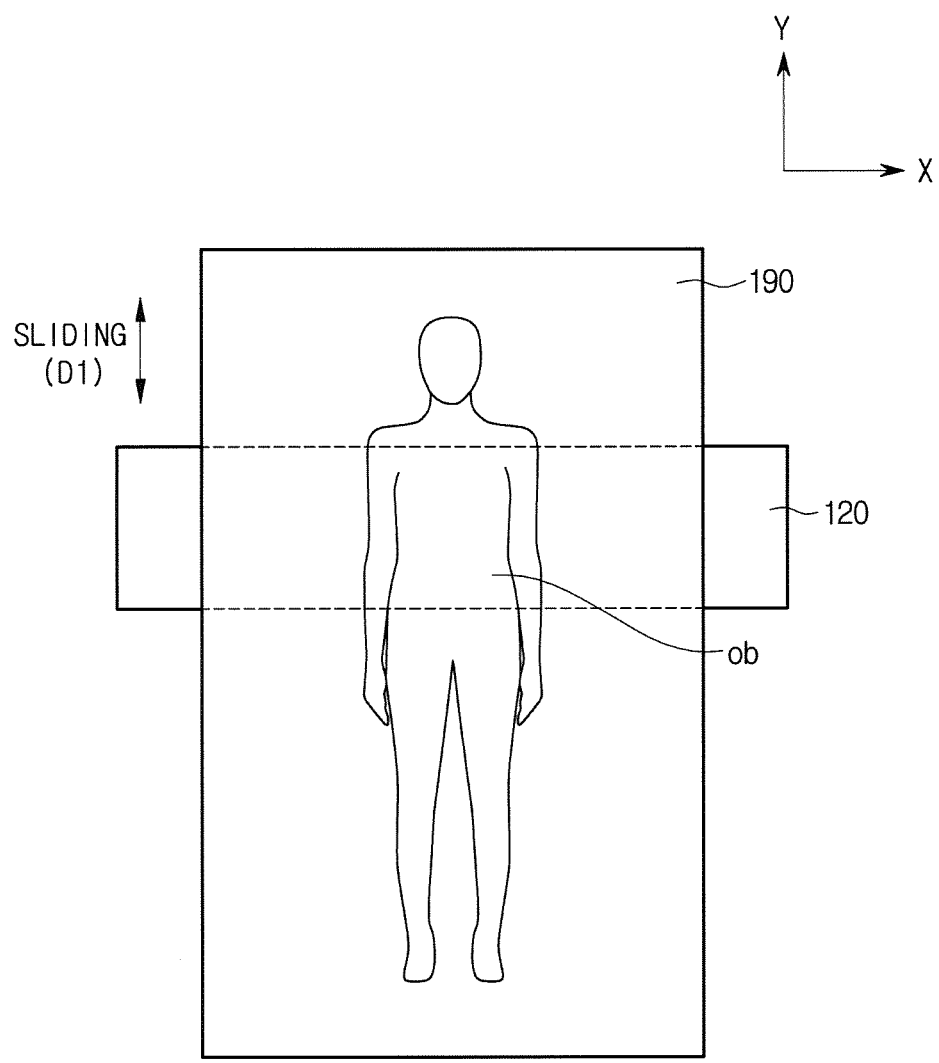
FIG. 2 illustrates a table with an object lying thereon, according to various embodiments of the present disclosure.
Figure 3:
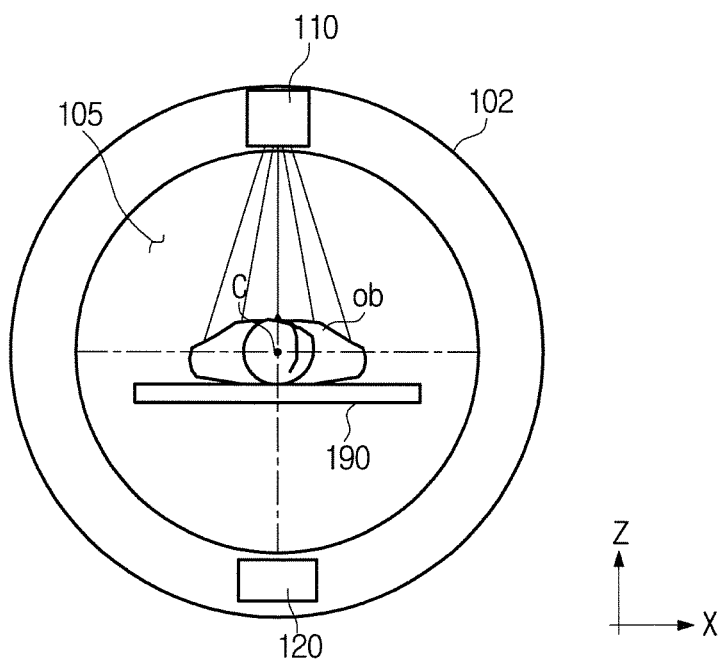
FIGS. 3 and 4 illustrate relations among an X-ray source, an X-ray detector, and an object positioned between the X-ray source and the X-ray detector, according to various embodiments of the present disclosure.
Figure 4:
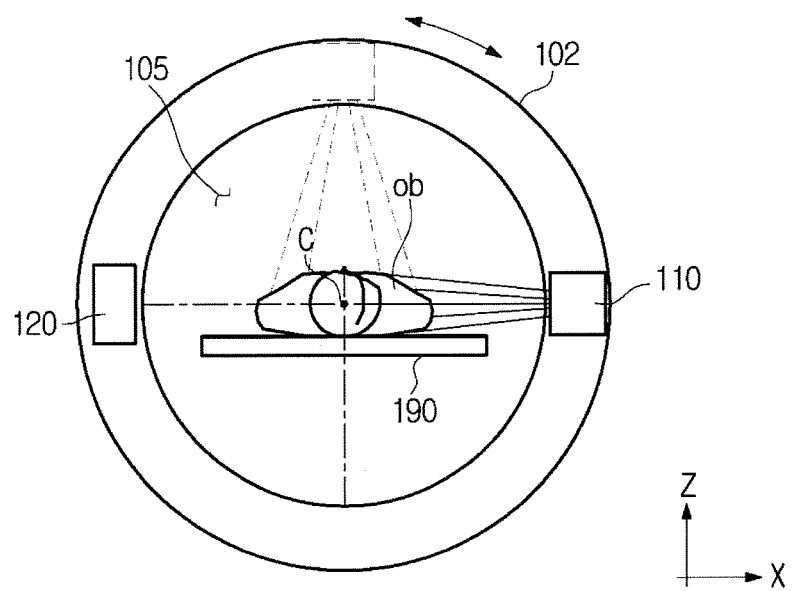
Figure 5:
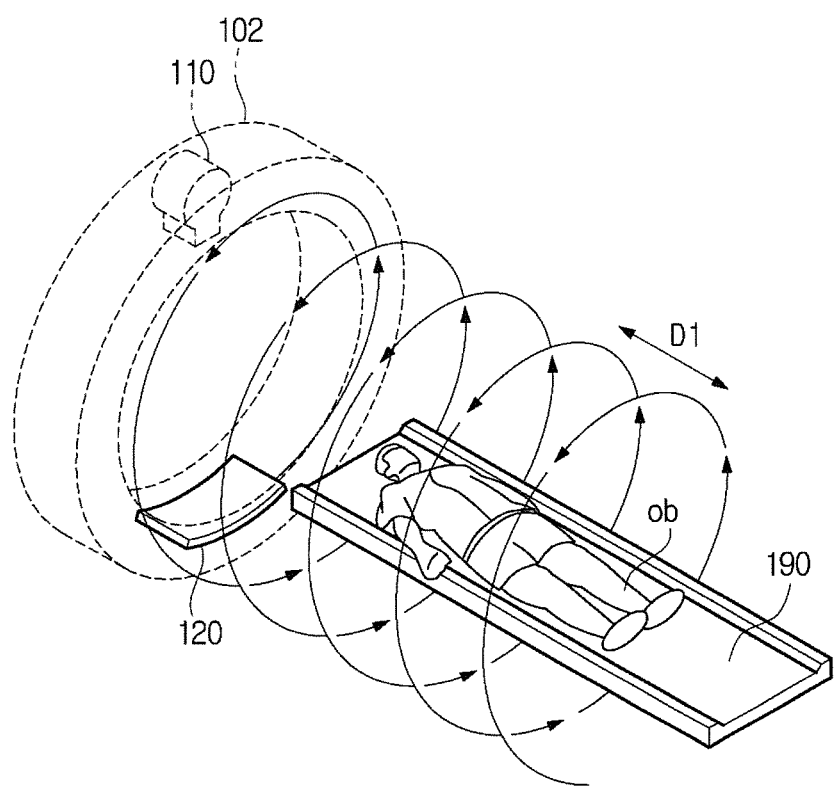
FIG. 5 illustrates a diagram for explaining an occasion when a scan is performed in a helical scanning method, according to various embodiments of the present disclosure.
Figure 6A:
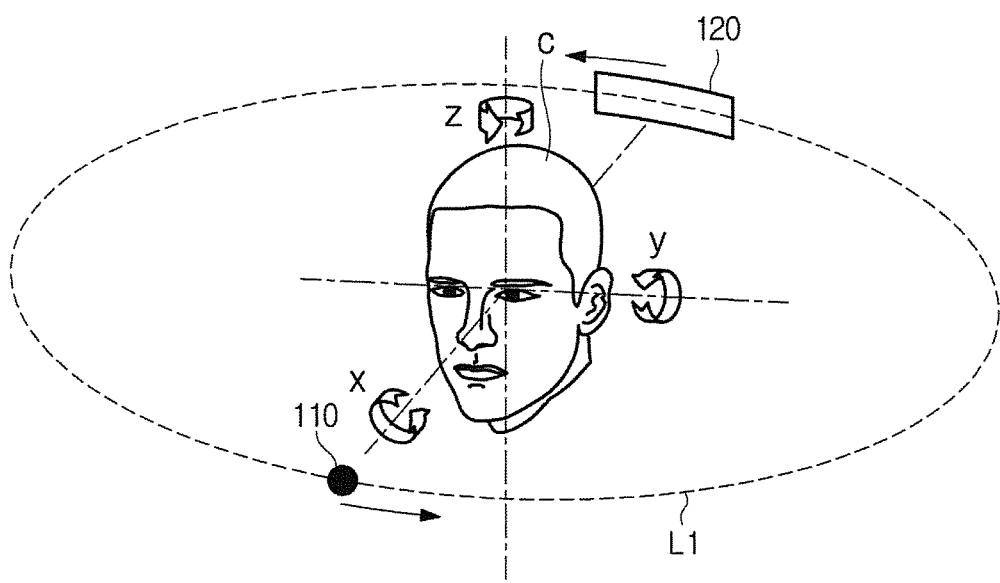
FIGS. 6A and 6B illustrates trajectories of a rotating X-ray source, according to various embodiments of the present disclosure.
Figure 6B:
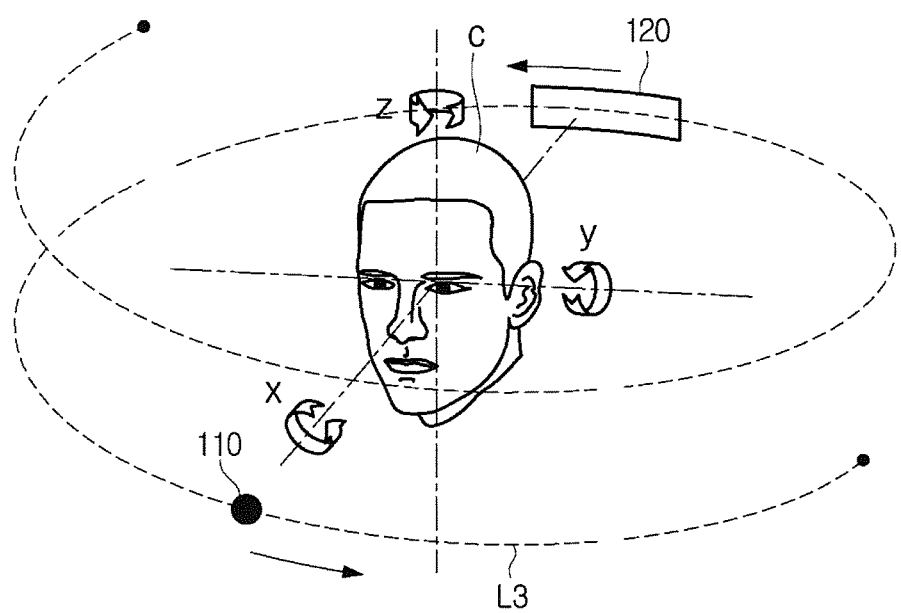
Figure 7A:
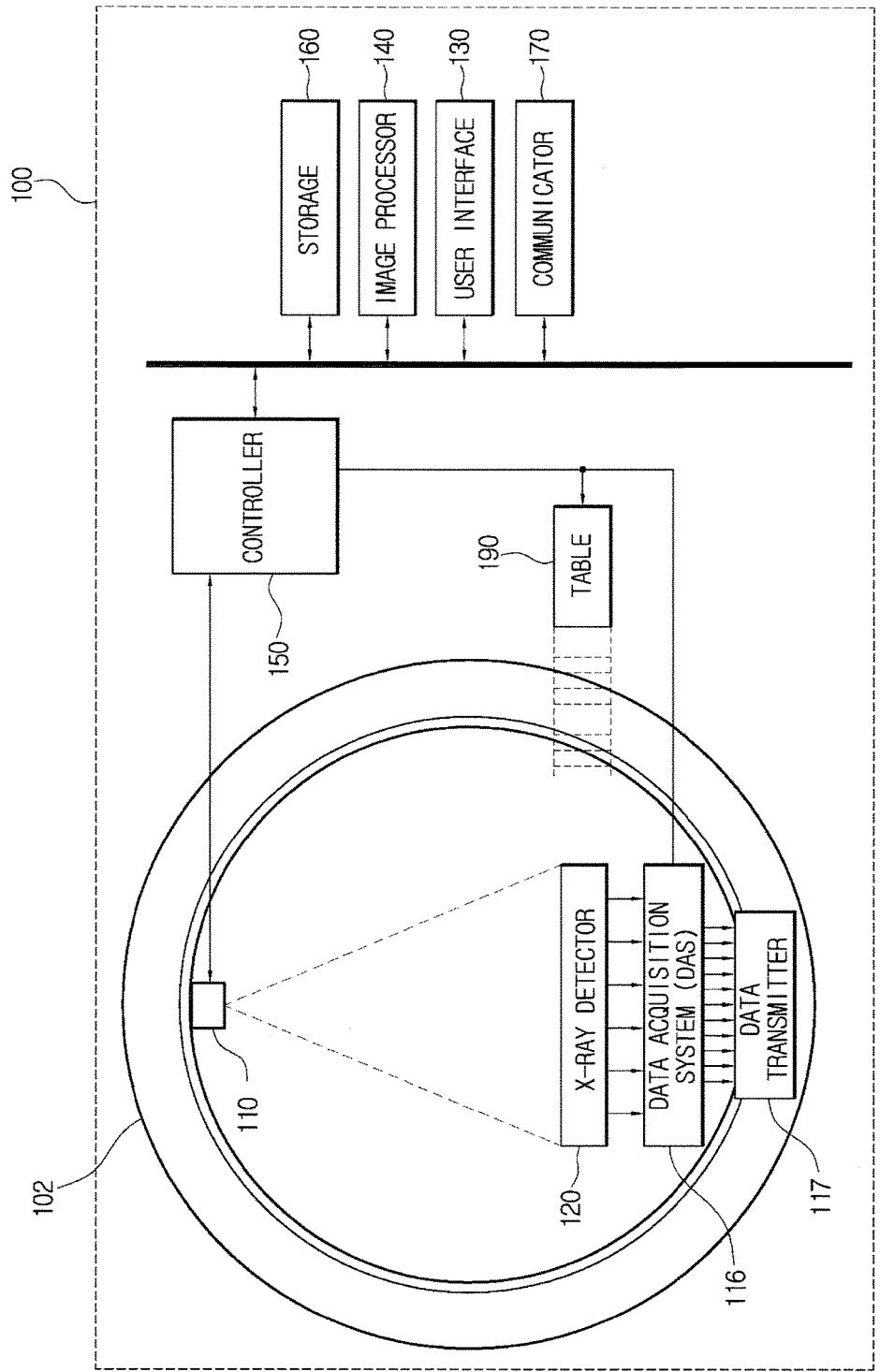
FIGS. 7A and 7B illustrate schematic control block diagrams of a medical imaging apparatus, according to various embodiments of the present disclosure.
Figure 7B:
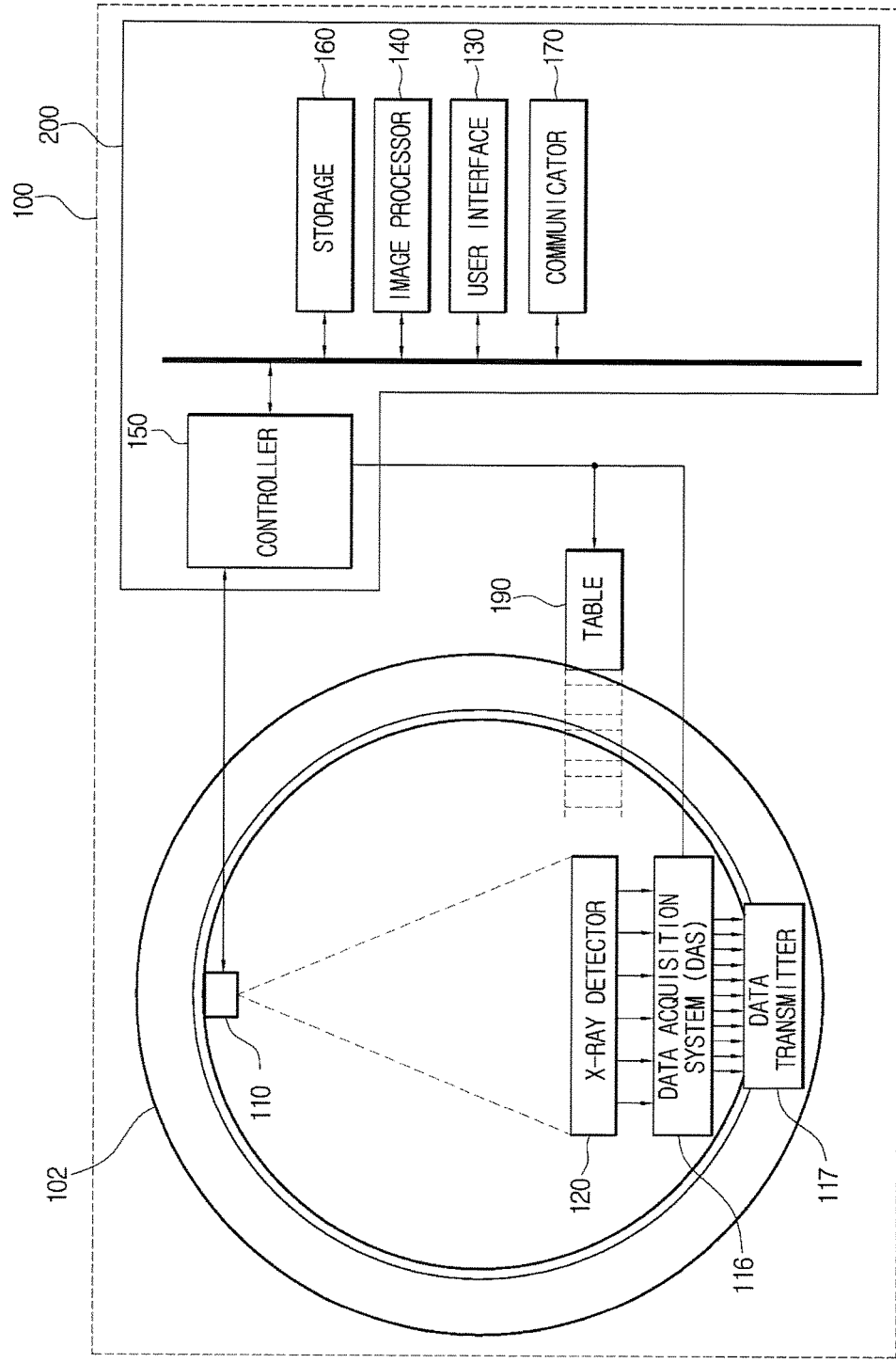

FIGS. 1A and 1B schematically show the exterior of an exemplary medical imaging apparatus, and FIG. 2 schematically shows a table with an object lying thereon, according to an embodiment of the present disclosure. FIGS. 3 and 4 schematically show relations among an X-ray source, an X-ray detector, and an object positioned between the X-ray source and the X-ray detector, according to an embodiment of the present disclosure. FIG. 5 is a diagram for explaining an occasion when a scan is performed in a helical scanning method, according to an embodiment of the present disclosure, and FIGS. 6A and 6B show trajectories of a rotating X-ray source, according to different embodiments of the present disclosure. FIGS. 7A and 7B are control block diagrams of a medical imaging apparatus, according to different embodiments of the present disclosure. The figures will now be described together to avoid overlapping explanation.

Referring to FIG. 1A, a medical imaging apparatus 100 may include a housing 101 where X-ray radiation and detection is performed, and a table 190 for transporting an object.

A cylindrical gantry 102 may be equipped in the housing 101. There may be an X-ray source 110 for irradiating X-rays and an X-ray detector 120 for detecting X-rays arranged to face each other inside the gantry 102.

An object ob may be placed between the X-ray source 110 and the X-ray detector 120. Specifically, the object ob may be put on the table 190, and the table 190 may enter to the inside of the gantry 102 (in D1 direction).

Referring to FIG. 1B, the medical imaging apparatus 100 may include a workstation 200 for performing operation control and image reconstruction of the medical imaging apparatus 100. The workstation 200 may also be called a host device or a console, and for convenience of explanation, the term 'workstation' may refer to any device for controlling general operation of the medical imaging apparatus 100. The workstation 200 will be described later in more detail.

Referring to FIG. 2, the object ob lies on the table 190 and is transported to the inside of the gantry 102. When a scan portion, i.e., a region of interest of the object ob is located in a scan position 105, the X-ray source 110 and X-ray detector 120 in the gantry 102 respectively irradiates and detects X-rays to scan the object ob while being rotated. The medical imaging apparatus 100 may then obtain a medical image based on the result of scanning.

Specifically, the gantry 102 may include a rotating frame (not shown), the X-ray source 110, the X-ray detector 120, a data acquisition circuit 116 (see FIG. 5), and a data transmitter 117 (see FIG. 5).

The X-ray source 110 refers to a device for generating and irradiating X-rays to the object ob. The X-ray source 110 may include a filter for filtering the irradiated X-rays.

The X-ray source 110 may irradiate X-rays in various ways. For example, the X-ray source 110 may irradiate X-rays in the form of three dimensional (3D) cone beams or two dimensional (2D) fan beams, without being limited thereto. In the following description, an occasion where X-rays are irradiated in the form of 3D cone beams will be taken as an example, without being limited thereto.

The X-ray detector 120 may refer to a device for detecting X-rays that has penetrated the object ob. The X-ray detector 120 may be arranged in the opposite of the X-ray source 110. As the table 190 enters to the inside of the gantry 102, the object ob may be placed between the X-ray source 110 and the X-ray detector 120. X-rays irradiated from the X-ray source 110 may then penetrate the object ob and may be detected by the X-ray detector 120.

For example, the X-ray detector 120 may detect the X-rays irradiated from the X-ray source 110 and generate an electric signal to correspond to the intensity of the detected X-rays. The X-ray detector 120 may be implemented in various forms. For example, the X-ray detector 120 may be implemented to have a flat form or a curved form, without being limited thereto.

The X-ray source 110 and X-ray detector 120 may be arranged on the opposite sides to each other, as shown in FIGS. 3 and 4, and obtain raw data by performing irradiation and detection of X-rays while being rotated 360 degrees through the rotating frame. In an embodiment, to scan a head part c of an object, the X-ray source 110 and the X-ray detector 120 may obtain raw data by X-ray irradiation and detection while being rotated 360 degrees around the head part c.

The medical imaging apparatus 100 may derive projection data by performing preprocessing on the raw data. This will be described in more detail later.

The object ob lies on the table 190 and is transported to the inside of the gantry 102. When a scan portion, i.e., a region of interest of the object ob is located in a scan position, the X-ray source 110 and X-ray detector 120 in the gantry 102 respectively irradiates and detects X-rays to scan the object ob while being rotated.

Scanning of the object ob may be performed while the table 190 is fixed as in an axial scan method, for example. In an embodiment, as the table 190 with the object ob lying thereon is sliding to the inside of the gantry 102 at a regular speed, a scan portion, i.e., a region of interest of the object ob may be located in a scan position. The table 190 may then be stopped, and the object ob may be scanned by the X-ray source 110 and the X-ray detector 120 in the gantry 102 irradiating and detecting X-rays, respectively, while being rotated.

The scanning method on the object ob is not limited thereto. The scan of the object ob may be performed while the table 190 is moving along a particular axis or while the table 190 is fixed but the X-ray source 110 and the X-ray detector are moving along a particular axis, as in the helical scanning method.

Referring to FIG. 5, one of the gantry 102 equipped with the X-ray source 110 and the X-ray detector 120 and the table 190 may be moved along D1 axis during a scan.

For example, while the X-ray source 110 and X-ray detector 120 are being rotated, the table 190 may be moved along the D1 axis at a constant speed. In this regard, the object ob may be scanned by the X-ray source 110 and X-ray detector 120 irradiating and detecting X-rays, respectively, while being rotated. As the scan is performed while the table 190 is being moved, the X-ray source 110 and X-ray detector 120 may perform scanning on the object ob while being helically rotated around the object ob, as shown in FIG. 5. In an embodiment, a scan time may be set to about 250 ms to about 1 second, without being limited thereto, depending on stability of the medical imaging apparatus 100.

However, as scanning is performed while the table 190 is being moved, the X-ray source, the X-ray detector 120, and the object ob may have motions caused by various factors.

For example, if the medical imaging apparatus 100 is not placed on a level floor, the table 190 or the gantry 102 of the medical imaging apparatus 100 might have motions while being moved.

The motion as herein used refers to a movement that deviates from what is set according to a scanning method. Due to this motion, not only a distance between the X-ray source 110 and the X-ray detector 120 but also distances between the X-ray source 110 and the object ob and between the X-ray detector 120 and the object ob may vary, causing artifacts to a medical image.

In another example, the gantry 102 equipped with the X-ray source 110 and the X-ray detector 120 may be moved while the table 190 is fixed. Accordingly, as the X-ray source 110 and the X-ray detector 120 are being moved along the D1 axis for scanning, the scanning may be performed while the X-ray source 110 and the X-ray detector 120 are being helically rotated, as shown in FIG. 5.

For example, in a case of a mobile CT device mainly used in operating rooms, as an example of the medical imaging apparatus 100, such a helical scanning method may often be used. The helical scanning method, however, may have low stability because of various factors, such as levelness of the floor on which the medical imaging apparatus 100 is placed, external pressure, etc., thereby having motions.

Accordingly, the distance between the X-ray source 110 and the X-ray detector 120 is more likely to vary, and so are the distances between the X-ray source 110 and the object ob and between the X-ray detector 120 and the object ob. The changes in distance cause artifacts to a medical image, thus requiring compensation. This will be described in more detail later.

In embodiments of the present disclosure, the medical imaging apparatus 100 may obtain raw data by performing a scan in the aforementioned various scanning methods, without being limited thereto.

For example, referring to FIG. 6A, the medical imaging apparatus 100 may obtain a medical image of a head part c of an object by irradiating X-rays onto the head part c of the object through the X-ray source 110. The X-ray source 110 and the X-ray detector 120 may obtain raw data from various views, i.e., at various scanning points of time or at various scanning angles, while facing each other and being rotated 360 degrees along a trajectory L1. In this case, not only the head part c of the object but any other part may be set to a region of interest in the medical image, without being limited thereto.

In another example, referring to FIG. 6B, the medical imaging apparatus 100 may obtain a medical image of the head part c of the object by helically rotating the X-ray source 110 to irradiate X-rays onto the head part c of the object. The X-ray source 110 and the X-ray detector 120 may obtain raw data at various scanning points of time or at various scanning angles, while being rotated along a trajectory L3.

A method for reconstructing a medical image from the raw data obtained along the trajectory L1 shown in FIG. 6A and a method for reconstructing a medical image from the raw data obtained along the trajectory L3 shown in FIG. 6B may or may not be the same.

For example, to reconstruct a medical image from the raw data obtained along the trajectory L3 shown in FIG. 6B, a well-known image processing process, such as 360 linear interpolation, 180 linear interpolation, etc., may be additionally required, without being limited thereto. A control block diagram of the medical imaging apparatus 100 will now be described.

FIGS. 7A and 7B are control block diagrams of medical imaging apparatuses, according to different embodiments of the present disclosure.

Referring to FIG. 7A, the medical imaging apparatus 100 may include the gantry 102, the X-ray source 110, the data acquisition circuit 116, the data transmitter 117, the X-ray detector 120, a user interface 130, an image processor 140, a controller 150, a storage 160, a communicator 170, and the table 190.

At least one of the image processor 140, the controller 150, the storage 160, and the communicator 170 may be integrated in a system on chip (SoC) embedded in the medical imaging apparatus 100. It is not limited to being integrated in one SoC because the medical imaging apparatus 100 may have more than one SoCs. The X-ray source 110, the X-ray detector 120, and the table 190 are the same as those described above, so the details will be omitted herein.

The table 190 may be moved in a certain direction (e.g., at least one of directions of x-, y-, and z-axis). The table 190 may be moved under the control of the controller 150. The controller 150 will be described later in more detail.

The data acquisition circuit or data acquisition system (DAS) 116 may be linked to the X-ray detector 120 wiredly or wirelessly, for collecting digital signals or digital data generated from the X-ray detector 120. The digital data may be wiredly or wirelessly sent to the image processor 140 through the data transmitter 117. The digital data to be sent is called raw data.

The user interface 130 may receive various control commands from the user to operate the medical imaging apparatus 100, and provide various information. The user interface 130 will be described later in more detail.

The image processor 140 may perform various processes to obtain medical images. For example, the image processor 140 may be implemented with a graphic processor and a graphic memory.

The image processor 140 may receive the raw data and perform preprocessing on the raw data. The preprocessing is a process required to obtain projection data, and may include, for example, a process for correcting irregular sensitivities among channels, a process for correcting a sudden decrease in signal intensity or a signal loss due to an X-ray absorbent material such as metal, or any other well-known processes required for obtaining the projection data.

The projection data may be a set of raw data obtained at one scanning angle. In other words, a set of raw data obtained at the same scanning angle for all the channels is called the projection data.

The image processor 140 may obtain the projection data at all scanning angles to generate a sinogram. That is, a set of projection data is called a sinogram, which may include, for example, projection data captured at various scanning angles ranging from 0 to 360 degrees of rotation angle of the X-ray source 110.

For example, the X-ray source 110 and the X-ray detector 120 facing each other are rotated 360 degrees to obtain raw data from 1440 views for 250 ms of scan time, i.e., at 1440 scan points of time. Specifically, raw data may be obtained in all directions at intervals of 0.25°, and a medical image may be created by applying a reconstruction scheme, such as a back projection process on the sinogram, which corresponds to a set of projection data obtained by performing the preprocessing process. The medical image as herein used may refer to an image implemented in 3D.

For example, the image processor 140 may reconstruct the medical image of an object using the obtained projection data. For example, the image processor 140 may create a 3D medical image by applying a certain process on the projection data, followed by a back projection process based on a Feldkamp, Davis and Kress (FDK) algorithm. While how to reconstruct a medical image by the back projection based on the FDK algorithm will be described below for example, other image reconstruction schemes may be applied in other embodiments.

The image processor 140 may create a medical image from the projection data through the back projection process based on the FDK algorithm. At this time, the object may move while X-rays are irradiated, i.e., during a scan. For example, the head part of the user may have motions during a scan. Accordingly, the motion of the object may cause artifacts unless the motion is compensated for, thereby failing to provide a correct medical image.

In an embodiment, the image processor 140 may thus calculate a motion parameter in creating a medical image from the obtained sinogram, and create a motion-compensated medical image by reflecting the calculated motion parameter.

The motion parameter as herein used may refer to a parameter that may represent an extent of motion of the object in a coordinate system. The coordinate system may include any kind of coordinate system, which may represent a motion of an object in coordinates.

For example, in a case of using the Cartesian coordinate system to represent coordinates in three orthogonal axes (x, y, and z axes), the motion parameter may be represented by angles and distances of the object with respect to the x, y, and z axes.

For example, the motion parameter may include six parameters: $Rx(\Psi)$, $Ry(\Phi)$ $Rz(\theta)$, Tx, Ty, and Tz. $Rx(\Psi)$ represents an angle the object is moved along the x-axis, $Ry(\Phi)$ represents an angle the object is moved along the y-axis, and $Rz(\theta)$ represents an angle the object is moved along the z-axis. Tx represents a distance the object is moved along the x-axis, Ty represents a distance the object is moved along the y-axis, and Tz represents a distance the object is moved along the z-axis.

Meanwhile, as described above, components of the medical imaging apparatus 100 may have motions during a scan, which may cause artifacts to a medical image. In this regard, the motion parameter may include not only the motion of the object itself but also a motion of a component of the medical imaging apparatus 100. Accordingly, the medical imaging apparatus 100 in an embodiment may minimize a possibility of causing artifacts to a medical image with the motion parameter that reflects not only the motion of the object but also the motion of a component of the medical imaging apparatus 100.

For example, in a case that the X-ray source 110 has a motion at a particular scan time or at a particular scan point of time, if it is assumed that there is no motion of the X-ray source 110, i.e., that the X-ray source 110 is fixed, but the motion of the X-ray source 110 is reflected as a motion of the object, even the motion of the X-ray source 110 may be reflected on a virtual trajectory.

In other words, if a component of the medical imaging apparatus 100 has a motion at a particular scan time or particular scan point of time, the motion of the component in the medical imaging apparatus 100 may be reflected as a relative motion of the object. In an embodiment, if the X-ray source 110 is moved +1 cm along the x-axis, the motion of the X-ray source 110 may be reflected by reflecting that the object is relatively moved −1 cm along the x-axis. Accordingly, if the location of the X-ray source 110 is moved +1 cm along the x-axis on the virtual trajectory to compensate for the motion of the object, the motion of the X-ray source 110 may be reflected on the virtual trajectory. This will be described in more detail later. The motion of the object as herein used includes not only a motion of the object itself but also a relative motion of the object reflecting a change in motion of a component of the medical imaging apparatus 100, and the motion parameter as will be described below may include not only the motion of the object but also a motion of a component of the medical imaging apparatus 100.

The motion parameter may further include parameter Tsd to represent a motion between the X-ray source 110 and the X-ray detector 120, in addition to the aforementioned six parameters. If a distance between the X-ray source 110 and the X-ray detector 120 changes, a magnifying power is changed in the back projection, causing artifacts to a reconstructed medical image. Accordingly, the image processor 140 may determine the motion parameter further including Tsd that represents a distance between the X-ray source 110 and the X-ray detector 120 and use the motion parameter in creating a sharper medical image.

If how much the object has been moved at each scan time or each scan point of time is known, i.e., if the motion parameter is determined, the image processor 140 may perform more accurate back projection by adjusting a back projection position based on the motion parameter. How to calculate the motion parameter will now be described.

The image processor 140 may determine the motion parameter from a medical image reconstructed from the projection data. In this regard, the image processor 140 may perform image reconstruction based on preset initial motion parameter values. The initial motion parameter values may be preset and stored in e.g., a graphic memory of the image processor 140. In an embodiment, an initial motion of an object is typically small, so the initial motion parameter values may all be set to '0'. As will be described below, the image processor 140 may provide a motion-compensated medical image of an object by determining motion parameter values and reconstructing a medical image using the determined motion parameter values.

In the following description, for convenience of explanation, a medical image created by applying a reconstruction scheme based on the preset initial motion parameter values is called a first medical image, and a medical image created by applying a reconstruction scheme based on the determined motion parameter values is called a second medical image.

When the image processor 140 reconstructs the first medical image through back projection, the more the motion, the lower the image quality of the first medical image. In the meantime, before the back projection process, a weighting process and a filtering process may be performed, which will be described later in more detail.

The back projection process based on the FDK algorithm is a calculation process for reconstructing the projection data that underwent the weighting process and the filtering process into a medical image, and is mainly used for obtaining a 3D medical image.

The 3D medical image refers to an image obtained by volume-rendering 3D volume data created based on a plurality of cross-sectional images from a certain point of time. For example, the image processor 140 may map and reconstruct the projection data captured at various angles into a 3D medical image. In this regard, the mapping is performed while a reference position of the back projection is being moved, and a value of when the clearest image is reconstructed may be determined as a motion parameter value at the corresponding scan point of time.

For example, the image processor 140 may perform mapping on the projection data obtained from 1440 views and determine a motion parameter value of when the 3D reconstructed medical image comes in the clearest one as a motion parameter value at the corresponding scan time or corresponding scan point of time.

Accordingly, the image processor 140 may determine a motion parameter value of when the clearest medical image is obtained as a motion parameter value representing a motion of the object at the corresponding scan time or scan point of time, while adjusting the motion parameter value.

The image processor 140 may reconstruct a motion-compensated second medical image by estimating image quality while adjusting the motion parameter value for the reconstructed first medical image, determining an optimum motion parameter value based on the estimation result, and updating the motion parameter value based on the optimum motion parameter value.

For example, the image processor 140 may determine a motion parameter value at a corresponding scan time or scan point of time based on resultant values from application of an image quality metric process. The image quality metric process as herein used refers to one of quantitative schemes for determining image quality of an image.

In an embodiment, the image processor 140 may apply the image quality metric process and determine the smallest resultant value as a motion parameter value at a corresponding scan time or scan point of time. Alternatively, the image processor 140 may apply the image quality metric process to the reconstructed first medical image, and determine a resultant value that meets a predetermined level as a motion parameter value at a corresponding scan time or scan point of time. For example, the image processor 140 may determine that a motion artifact of the object is minimized when a value resulting from application of the image quality metric process for the first medical image is minimized or maximized, and determine the resultant value as a motion parameter value at the corresponding scan time or scan point of time.

In this case, the image processor 140 may set a variable to the motion parameter, set a target of the resultant value, and then apply the image quality metric process. The variable may be set to have 6 or 7 motion parameters, without being limited thereto.

For example, the image processor 140 may set an entropy to be the resultant value, apply the image quality metric process, and determine a value resulting from the application of the image quality metric process, i.e., a motion parameter value of when the entropy value is minimized, as a motion parameter value at the corresponding scan time. In other words, the image processor 140 may determine a motion parameter value of when the entropy is minimized as a motion parameter value at the corresponding scan time.

In another example, the image processor 140 may set a degree of sharpness or gradient value in an edge area among areas that represent an object in the first medical image to a target of the resultant value, and then determine a motion parameter value of when the resultant value is maximized as a motion parameter value at the corresponding scan time or scan point of time.

Meanwhile, as the motion of the object is continuous and varies every moment, a motion parameter value of the object may vary by scan time or scan point of time. Thus, a motion parameter value needs to be determined at each scan time or scan point of time to reconstruct a more correct image, which, however, may increase an amount of computation.

Accordingly, the image processor 140 in an embodiment of the present disclosure might determine a motion parameter value at every scan time, but it may set one or more control points by evenly dividing the scan time and determine motion parameter values at the set control points. The image processor 140 may then draw lines that link the motion parameter values at the control points, thereby forming a graph of the motion parameter value over a scan time. The control point as herein used refers to a particular time of the scan time or a particular scan point among the scan points of time.

For example, the image processor 140 may set N or more control points, where N≥1, in the entire scan time or all the scan points of time, determine motion parameter values at the respective control points, and form a graph by linking the respective motion parameter values. Accordingly, the image processor 140 may determine a parameter value corresponding to each scan time or each scan point of time from the graph, and reconstruct more correct image by adjusting the position for back projection based on the parameter value.

The image processor 140 may repeatedly perform the operation of determining the motion parameter value, as described above, at particular points, and replace or update the initially set motion parameter value with the determined motion parameter value, thereby reconstructing more correct image. Accordingly, the medical imaging apparatus 100 in an embodiment may determine the motion of an object in a medical image and then provide a motion-compensated medical image of the object, without need for determining the motion of the object through an extra device.

Figure 8A:
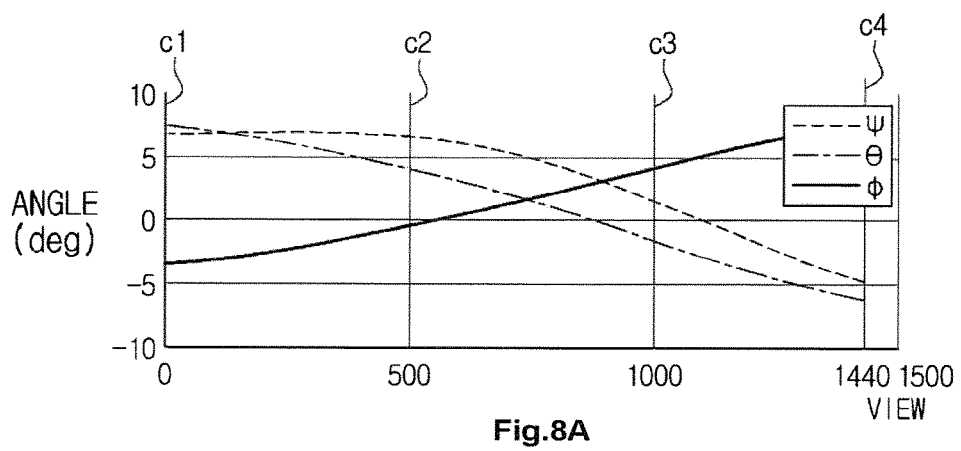
FIGS. 8A and 8B illustrate graphs of motion parameters during a scan time, according to various embodiments of the present disclosure.
Figure 8B:
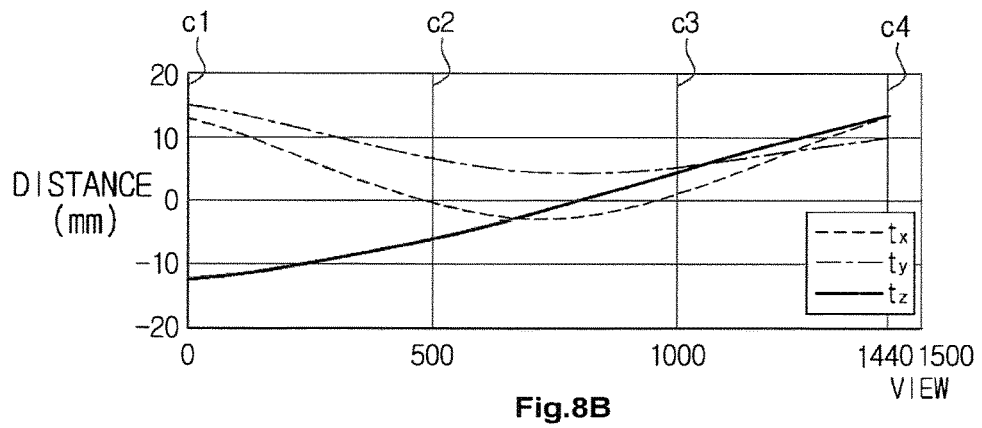

FIGS. 8A and 8B show graphs of motion parameters during a scan time, according to an embodiment of the present disclosure. Referring to FIGS. 8A and 8B, the image processor 1400 may set 4 control points C1, C2, C3, and C4, and determine motion parameter values at the respective control points by applying an image quality metric process. The image processor 1400 may then determine 6 motion parameter values at each control points, and perform approximation based on the motion parameter values to form graphs as in FIGS. 8A and 8B.

In other words, the image processor 140 may determine motion parameter values corresponding to a particular time in the entire scan time through an image quality metric process, and then perform approximation based on the determined motion parameter values to form a graph. The image processor 140 may then calculate motion parameter values at each scan time or each scan point of time from the graph, and create a more correct second medical image based on the calculated motion parameter values.

The more the number of the control points, the higher the accuracy of the graph. In this regard, the number of the control points and gaps between the control points may be preset. For example, the number of the control points may be set to a particular number in advance, or may be set in advance to be determined in proportion to the number of views or scan times. The gaps between the control points may be the same according to the number of the scan points of time or scan times. Data about the settings of the control points may be stored in a graphic memory in advance, and so the image processor 140 may set at least one of the number of the control points and the gap between the control points based on the data stored in the graphic memory.

In another example, the number of the control points and gaps between the control points may be set by the user in person. In an embodiment, the user may set at least one of the number of the control points and the gap between the control points through the user interface 130. Upon reception of information about at least one of the number of the control points and the gap between the control points set by the user from the user interface 130, the image processor 140 may determine motion parameter values at the corresponding control points based on the information, form a graph through approximation with the determined motion parameter values, and create the second medical image using the graph.

Accordingly, the medical imaging apparatus 100 in an embodiment may allow the user to set the control points in person according to priorities of precision and reconstruction speed for the medical image, thereby increasing the degree of freedom of the user. How to create a motion-compensated second medical image based on the motion parameter values will now be described.

For example, from the determination of the motion parameter value, it may be determined that the object has been moved +1 cm along the x-axis at a particular scan time or scan point of time. In order to compensate for the motion of the object, the position of the X-ray source 110 may be moved −1 cm along the x-axis at the particular scan time or scan point of time to relatively compensate for the motion of the object.

In this case, the motion of the object may be caused by at least one of the motion of the object itself and a motion of a component of the medical imaging apparatus 100 at a particular scan time or scan point of time.

Accordingly, if it is determined based on the motion parameter value that the object has been moved +1 cm along the x-axis at the particular scan time or scan point of time, it may be that the object itself might have moved +1 cm or the X-ray source 110 might have been moved −1 cm. Otherwise, the object might have moved +2 cm while the X-ray source 110 might have been moved −1 cm. In this regard, there is no need to represent which of the object and the X-ray source 110 has been moved to what extent, but both the motions of the object and the X-ray source 110 have only to be reflected. In this case, to compensate for the motion of the object, the position of the X-ray source 110 may be moved −1 cm on the virtual trajectory at the particular scan time or scan point of time to compensate both for the motion of the object itself and for the relative motion of the object.

The image processor 140 may create a virtual trajectory of the X-ray source 110 based on the motion parameter value. The virtual trajectory of the X-ray source 110 refers to a trajectory created by reflecting the motion of the object in a fixed position on a trajectory of the X-ray source 110. In other words, the virtual trajectory of the X-ray source 110 is not a trajectory the X-ray source has actually moved for a scan but a trajectory virtually created by reflecting changes in position of the object on the trajectory of the X-ray source 110.

Accordingly, the virtual trajectory of the X-ray source 110 compensates for the motion of the object, so if the object has a motion during a scan, there is a difference between the virtual trajectory and the actual trajectory the X-ray source 110 is rotated for scanning. It is assumed that not only the X-ray source 110 is rotated along the virtual trajectory but also the X-ray detector on the opposite side of the X-ray source 110 is rotated along the virtual trajectory.

The image processor 140 may create a virtual trajectory L2 of the X-ray source 110 in a virtual space by reflecting the motion of a head part c of the object, as shown in FIG. 9A. Accordingly, the image processor 140 may create a motion-compensated second medical image by resetting a distance between the X-ray source 110 and the head part c and a distance between the X-ray source 110 and the X-ray detector 120, based on the virtual trajectory L2 of the X-ray source 110.

Furthermore, in a case that a scan is performed according to a helical scanning method, the image processor 140 may create a virtual trajectory L4 of the X-ray source 110 in a virtual space by reflecting a motion of the object, as shown in FIG. 9B. The virtual trajectory L4 in the virtual space may reflect not only the motion of the head part c of the object itself, but also the motion of a component of the medical imaging apparatus 100, such as the X-ray source 110 or the X-ray detector 120. In other words, the virtual trajectory L4 may be created by compensating for the motion of the head part c of the object itself, or by compensating for the motion of a component of the medical imaging apparatus 100, or by compensating for both the motions.

Figure 10:
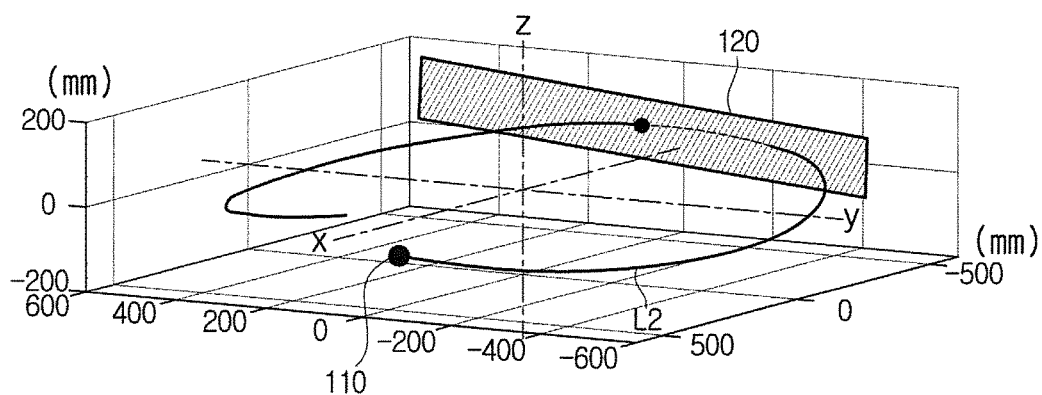
FIG. 10 illustrates a virtual trajectory of an X-ray source in the Cartesian coordinate system, according to various embodiments of the present disclosure.

FIG. 10 represents a virtual trajectory of the X-ray source 110 in the Cartesian coordinate system, according to an embodiment of the present disclosure. As described above, even though an actual moving trajectory of the X-ray source 110 may be the trajectory L1, a virtual trajectory reflecting the motion of an object may be changed to the virtual trajectory L2 shown in FIG. 9. The image processor 140 may represent the virtual trajectory L2 of the X-ray source 110 in the Cartesian coordinate system, as shown in FIG. 10. It is assumed that the X-ray detector 120 is placed on the opposite side of the X-ray source 110 and rotated along the virtual trajectory.

Before performing a back projection process, the image processor 140 may perform a weighting process and filtering process based on the FDK algorithm by reflecting the virtual trajectory of the X-ray source 110.

The weighting process as herein used refers to a process for reconstructing an intensity value per projection data. An extent to which the intensity value is reconstructed depends on the distance between the X-ray source 110 and the X-ray detector 120.

The distance between the X-ray source 110 and the X-ray detector 120 on the virtual trajectory may be different from that on the actual trajectory. Due to the continuous movements of the object, the distance between the X-ray source 110 and the X-ray detector 120 on the virtual trajectory and that on the actual trajectory may be different at each scan time or scan point of time.

Accordingly, the image processor 140 in an embodiment may create the second medical image with intensity values about the object reconstructed more accurately, by calculating a distance between the X-ray source 110 and the X-ray detector 120 based on the virtual trajectory of the X-ray source 110 and performing the weighting process based on the calculation. In this regard, the image processor 140 in an embodiment may more accurately reconstruct the intensity value about the object in the second medical image by calculating a distance between the X-ray source 110 and the X-ray detector 120 on the virtual trajectory of the X-ray source 110 over scan points of time or scan time, and performing the weighting process based on the calculation.

In another embodiment, the image processor 140 may perform the weighting process using one of the motion parameters, TSD. Specifically, without need to calculate the distance between the X-ray source 110 and the X-ray detector 120 from the virtual trajectory, the image processor 140 may determine 7 motion parameters including TSD by applying an image quality metric process.

The image processor 140 may also perform a filtering process based on the FDK algorithm before performing the back projection process. In general, the filtering process is performed with respect to the direction of a row of the X-ray detector 120. However, if filtering is performed with respect to the direction of the row of the X-ray detector 120 even when the object has had a motion, shading may occur to a medical image, failing to attain sharpness of the medical image. Accordingly, the image processor 140 may perform the filtering process by setting a moving direction, i.e., tangential direction of the X-ray source 110 to a filtering direction based on the virtual trajectory.

Figure 11A:
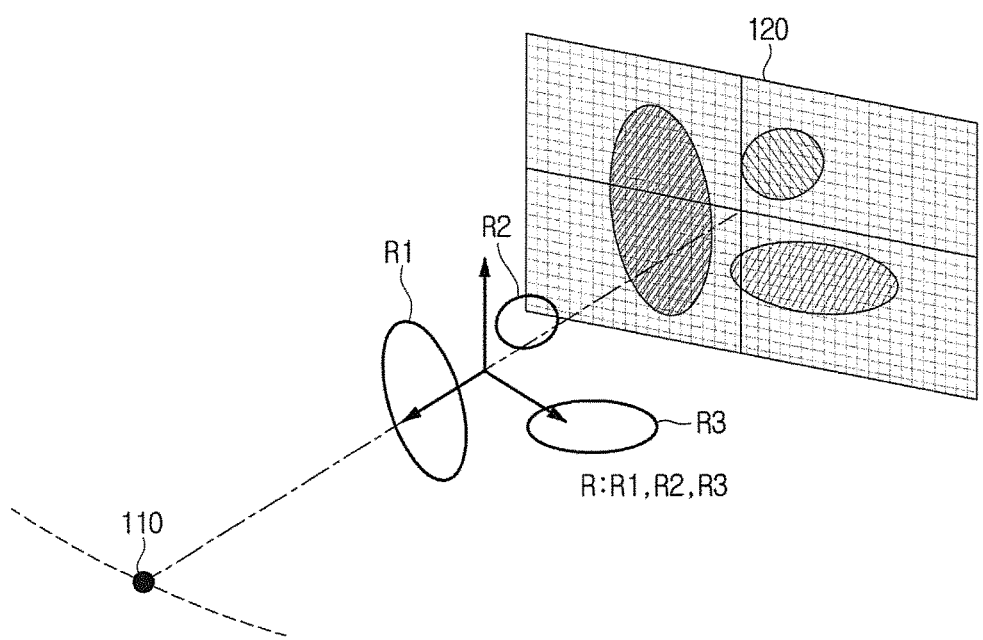
FIGS. 11A, 11B, and 11C illustrate diagrams for explaining occasions when a filtering direction is set to a tangential direction of an X-ray source, according to various embodiments of the present disclosure.
Figure 11B:
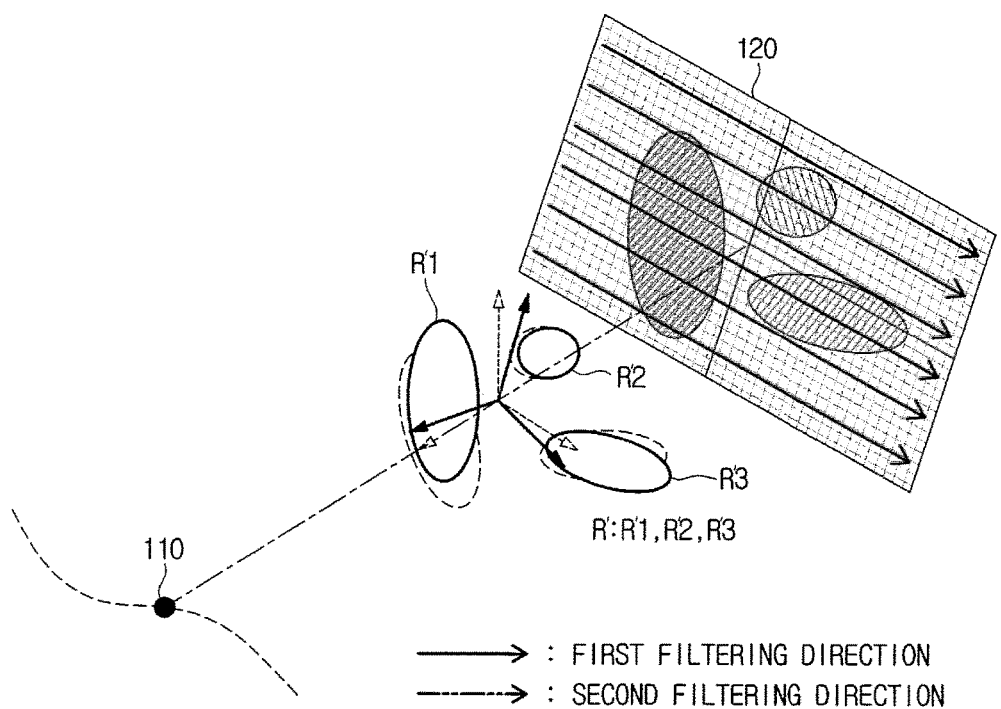
Figure 11C:
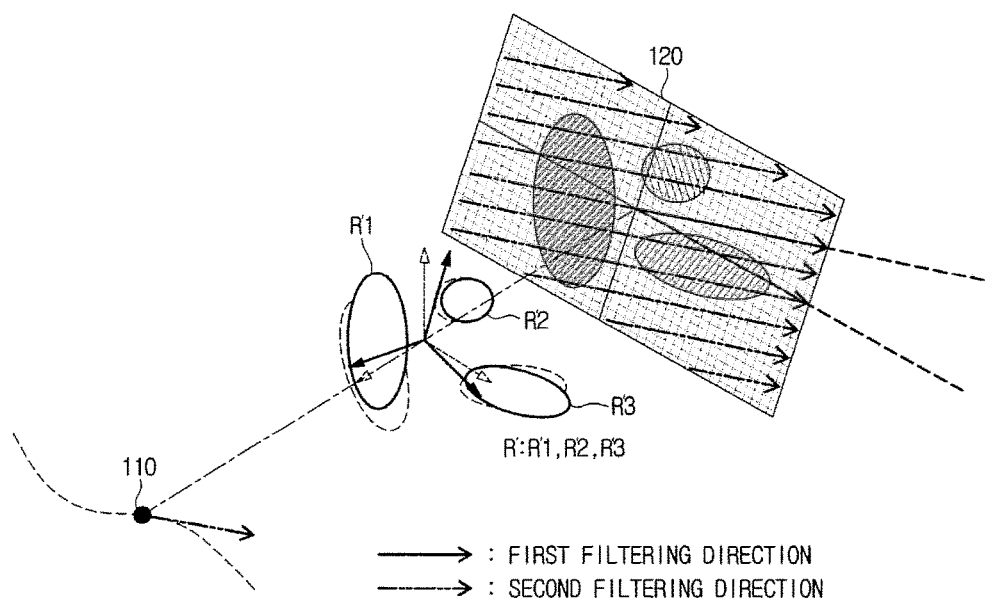

FIGS. 11A, 11B, and 11C show diagrams for explaining occasions when a filtering direction is set to a tangential direction of an X-ray source, according to different embodiments of the present disclosure.

First, FIG. 11A shows a region of interest R of an object on an actual trajectory of the X-ray source 110, not reflecting motions. Referring to FIG. 11A, as described above, the X-ray source 110 may irradiate X-rays onto an object while being rotated 360° along a rotation trajectory.

The X-ray detector 120 is placed on the opposite side of the X-ray source 110 and detects X-rays irradiated from the X-ray source 110. If the object is motionless during a scan, the image processor 140 has only to perform a filtering process by setting the direction of a row of the X-ray detector 120 shown in FIG. 11A to a filtering direction.

However, the object may have a motion during a scan time, and a region of interest R' of the object at a particular point of time may be located as shown in FIG. 11B. In this case, the image processor 140 may create a virtual trajectory of the X-ray source 110 as described above. The image processor 140 may determine that the X-ray source 110 and the X-ray detector 120 are located on the virtual trajectory at a particular scan point of time in the same directions and positions as shown in FIG. 11B.

In this case, if the image processor 140 sets a filtering direction to be a first filtering direction shown in FIG. 11B, i.e., the direction of a row of the X-ray detector 120, and then performs a filtering process, shading may occur to a reconstructed medical image. Furthermore, values of intensities in the same area in the medical image may not be even, making it difficult to make a correct diagnosis of the region of interest of the object.

Accordingly, the image processor 140 in an embodiment may perform the filtering process by setting the filtering direction to be a tangential direction of the X-ray source 110, i.e., a second filtering direction, as shown in FIG. 11C. The image processor 140 may then create a 3D medical image with values of intensities reconstructed more accurately.

Meanwhile, a curvature of the center in a domain to perform back projection needs to be taken into account. For example, if an X-ray detector in a curved form is used, the curvature of the X-ray detector needs to be reflected. Especially, if a tangential direction of the X-ray source 110 on the virtual trajectory is set to the filtering direction, the curvature may keep changing. Accordingly, if the curvature of the center along the virtual trajectory keeps changing, the curvature of the corresponding center needs to be taken into account, which makes calculations complicated.

In this case, a back projection process based on an FDK algorithm has preset calculation methods for flat and curved forms. Accordingly, the image processor 140 in an embodiment may perform the back projection process based on the FDK algorithm to be able to reconstruct the second medical image without complicated calculation even if the curvature of a center of a domain in which the back projection is performed is changed by a change in filtering direction.

Meanwhile, if there is a big difference between a preset initial motion parameter value and a motion of the object, an amount of calculation and time required to replace or update the motion parameter value may increase. For example, in a case that the object has a lot of motions during a scan, if the initial motion parameter values are set to '0', not only a large amount of calculation but also a long time may be required to replace or update the initial motion parameter values with accurate motion parameter values by performing the aforementioned process on the first medical image.

Figure 12:
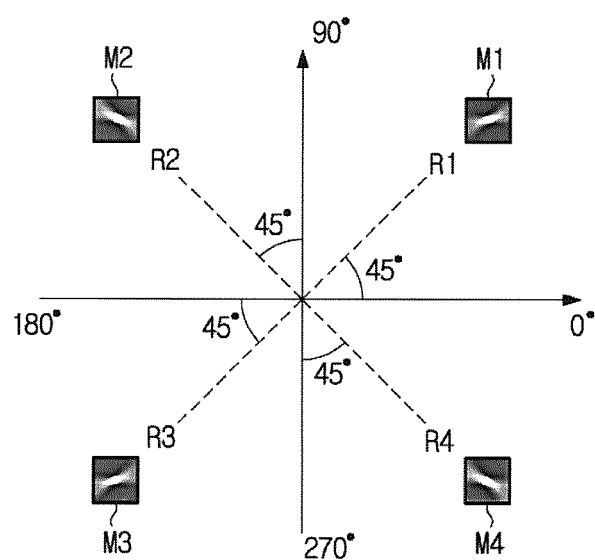
FIG. 12 illustrates a diagram for explaining how to determine template partial medical images and initial motion parameter values at a reference point, according to various embodiments of the present disclosure.
Figure 13A:
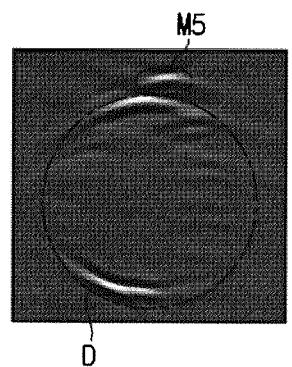
FIG. 13A illustrates a partial medical image including an object and a marker, according to various embodiments of the present disclosure.
Figure 13B:
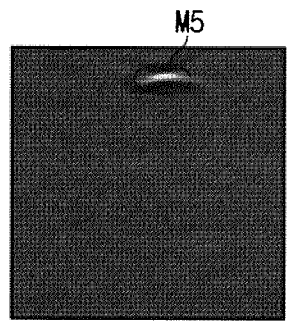
FIG. 13B illustrates a partial medical image on which masking is processed, according to various embodiments of the present disclosure.
Figure 14:
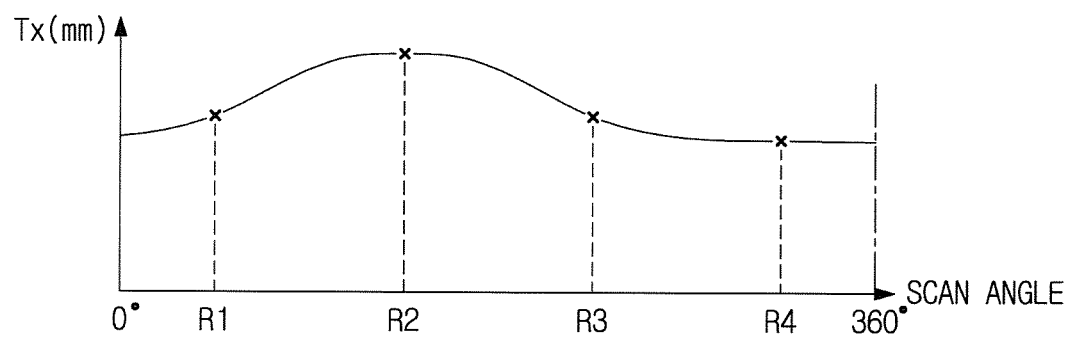
FIG. 14 illustrates a graph of initial motion parameter values formed by using initial motion parameter values at reference points, according to various embodiments of the present disclosure.

To overcome this problem, the image processor 140 in an embodiment may reduce the required amount of calculation and time by determining initial motion parameter values that reflect a motion of the object to some extent with a marker and then performing the aforementioned process based on the determination to determine an accurate motion parameter values. How to determine the initial motion parameter value will now be described. The embodiments as described above and those as will be described later may be practiced without the method for determining the initial motion parameter value, and there are no limitations on the embodiments. FIG. 12 is a diagram for explaining how to determine template partial medical images and initial motion parameter values at reference points, according to an embodiment of the present disclosure, FIG. 13A schematically shows a partial medical image including an object and a marker, according to an embodiment of the present disclosure, and FIG. 13B schematically shows a partial medical image on which a masking process is performed, according to an embodiment of the present disclosure. FIG. 14 shows a graph of initial motion parameter values formed with initial motion parameter values at reference points, according to an embodiment of the present disclosure. The figures will now be described together to avoid overlapping explanation.

For example, during a scan, a marker may be attached to the object, and thus a reconstructed medical image may include not only the scanned part of the object but also the marker. The marker may be implemented with a material that has no or little influence on examination of the scan portion of the object.

For example, the marker may be implemented with water, acrylic materials, synthetic resins, etc., without being limited thereto. Furthermore, the marker may further include a sponge for covering the aforementioned material. This makes the marker and the object separated more than a certain distance from each other in the reconstructed medical image, thereby identifying them more easily.

There are no limitations on the form and size of the marker to be implemented. Depending on features of scan portions of the object, it may be difficult to identify the marker from the scan portion of the object. To overcome this problem, the maker may be implemented in various sizes, and the user may select a proper marker for a scan portion of the object and attach the marker onto the object. Alternatively, the image processor 140 may identify the marker included in a partial medical image through a masking process. This will be described in more detail later.

The marker may be attachable to any portion of the object without limitations. For example, if a scan portion of the object corresponds to the head, the marker may be attached on the nose or ear of the object, without being limited thereto.

The image processor 140 may determine initial motion parameter values that reflect the motion of the object by comparing a template medical image obtained from a stored sinogram and a medical image reconstructed by scanning the object with a marker attached thereon to identify the marker included in the reconstructed medical image, and then determining initial motion parameter values based on a change in position of the marker.

The storage 160 may have stored template medical images reconstructed from raw data obtained by scanning the marker. The template medical images may include a plurality of template partial medical images divided by scan time, scan point of time, or scan angle. The template medical image may be created by the medical imaging apparatus 100 and stored in the storage 160, or created by an external device and stored in the storage 160. Alternatively, the template medical image may be stored in the external device, and the controller 150 may control the communicator 170 to receive the template medical image from the external device. In the following description, it is assumed that the template medical image is created by the image processor 140, for convenience of explanation.

For example, the image processor 140 may create template partial sinograms by dividing raw data obtained at all scan angles or scan points of time by a range of particular scan points of time or a range of particular scan angles. In other words, the image processor 140 may divide the entire scan points of time or entire scan angles by C (C≥2) ranges of particular scan points of time or particular scan angles, and create template partial sinograms based on the raw data in the respective ranges.

In an embodiment, assuming that a scan of the X-ray source 110 begins at a position of 0°, the image processor 140 may create a first template partial sinogram based on raw data obtained within an angle ranging from 0° to 90° (non-inclusive) clockwise or counterclockwise, and create a second template sinogram based on raw data obtained within an angle ranging from 90° to 180° (non-inclusive). Furthermore, the image processor 140 may create a third template partial sinogram based on raw data obtained within an angle ranging from 180° to 270° (non-inclusive), and create a fourth template sinogram based on raw data obtained within an angle ranging from 270° to 360° (non-inclusive).

The image processor 140 may then reconstruct template partial medical images from the respective template partial sinograms, and the markers appearing in the template partial medical images may have different forms.

For example, as shown in FIG. 12, the forms of the markers in the first to fourth template partial medical images M1, M2, M3, and M4 may be different. The first to fourth template partial medical images M1, M2, M3, and M4 have markers of a spherical form, but the figure of the marker may not be limited thereto and implemented in any other form.

The image processor 140 may perform a scan on the object with the marker attached thereon, and reconstruct a plurality of partial medical images divided according to a range of particular scan points of time or a range of particular scan angles, as described above. Accordingly, the image processor 140 may identify the marker by comparing the template partial medical image and the figure of the marker appearing in the partial medical image. In other words, the image processor 140 may distinguish the object and the marker included in the partial medical image based on the stored template partial medical image.

In order to identify the marker more correctly, the image processor 140 may perform masking on the partial medical image. For example, FIG. 13A schematically shows a partial medical image including an object and a marker, according to an embodiment of the present disclosure, and FIG. 13B schematically shows a partial medical image with the masked object.

The partial medical image shown in FIG. 13A may include a scan portion D of the object and a marker M5. The image processor 140 may create a partial medical image that includes only the marker M5 by masking the scan portion D of the object, as shown in FIG. 13B. The image processor 140 may identify the marker more easily by comparing the partial medical image subject to the masking process shown in FIG. 13B and the template partial medical image. In addition, if it is determined to have a difficulty distinguishing a scan portion of the object from the marker, the user may attach, but not exclusively, a proper marker onto the scan portion of the object as described above.

The image processor 140 may determine initial motion parameter values based on a change in position of the marker in the partial medical image. If the object has a motion, the marker attached onto the object is also moved. Accordingly, the image processor 140 may determine initial motion parameter values by tracking the position of the marker and reflecting the motion of the object.

For example, the position of the marker appearing in the first partial medical image may be different from positions of the marker appearing in the second to fourth partial medical images. The image processor 140 may determine an initial motion parameter value based on a relative change in position of the marker in the partial medical image.

Since the motion of the object is continuous, it may vary at every scan point of time or every scan time. In this case, determining the motion parameter value at every scan point of time or every scan time may cause an overload of calculation.

Accordingly, although the image processor 140 may determine the initial motion parameter value at every scan point of time or every scan angle, it may set a reference point for each partial medical image and determine the initial motion parameter value only at the set reference point, thereby efficiently controlling an amount of calculation.

For example, in the case of obtaining the first to fourth partial medical images by dividing the scan angle 360° by four, as described above, the image processor 140 may set first to fourth reference points R1, R2, R3, and R4 to 45°, 135°, 225°, and 315° in the first to fourth partial medical images, respectively.

In an embodiment, the image processor 140 may determine an initial motion parameter value at the first reference point R1 by tracking a change in position of the marker between the first and second partial medical images, and determine an initial motion parameter value at the second reference point R2 by tracking a change in position of the marker between the second and third partial medical images. In this way, the image processor 140 may determine initial motion parameter values at the third and fourth reference points.

The image processor 140 may determine the initial motion parameter values by comparing changes in position of the marker at the respective reference points, and then create a graph about the initial motion parameter values by linking the initial motion parameter values.

For example, referring to FIG. 14, the image processor 140 may determine Tx that represents a distance the object has moved along the x-axis at each of the reference points R1, R2, R3, and R4, and link them with lines to form a graph about Tx. The image processor 140 may also determine other initial motion parameter values in the same way.

The image processor 140 may then use the graph about the initial motion parameter values in determining correct motion parameter values. For example, the image processor 140 may determine motion parameter values from the first medical image based on the graph about the initial motion parameter values.

The image processor 140 may use both the motion parameter values at control points and the graphs about the initial motion parameter values to replace or update the motion parameter values with correct values. If it is determined that the motion of the object is small, the image processor 140 may set initial motion parameter values to '0', and then replace or update the motion parameter values from '0' to correct values by only using the graph about the motion parameter values at control points, without being limited thereto.

The medical imaging apparatus 1 may include the controller 150. The controller 150 may be implemented with a computational device, such as a processor.

The controller 150 may control general operation of the medical imaging apparatus 100. For example, the controller 150 may generate control signals to control the components of the medical imaging apparatus 100.

In an embodiment, the controller 150 may control operation of the X-ray source 110 and X-ray detector 120 based on control commands input through the user interface 130 to obtain raw data at various angles, without being limited thereto.

In another embodiment, the controller 150 may control the data acquisition circuit 116 with a control signal to deliver the raw data obtained by the X-ray detector 120 to the image processor 140. In addition, the controller 150 may control operation of the table 190 with a control signal to transport an object to the inside of the bore, without being limited thereto. The controller 150 may also provide acquired medical images to the user through the user interface 130, without being limited thereto.

The medical imaging apparatus 100 may include the storage 160.

The storage 160 may be implemented with a storage medium in a type of at least one of flash memory, hard disk, multimedia card micro type memory, card type memory (e.g., SD or XD memory), random access memory (RAM), static random access memory (SRAM), read-only memory (ROM), electrically erasable programmable read-only memory (EEPROM), programmable read-only memory (PROM), magnetic memory, magnetic disk, and optical disk. It is, however, not limited thereto, but may be implemented in any other form known in the art.

For example, the storage 160 may store various data associated with a method for controlling the operation of the medical imaging apparatus 100. Accordingly, the controller 150 may use the data stored in the storage 160 to control the operation of the medical imaging apparatus 100. In another example, the storage 160 may store medical images reconstructed by the image processor 140 and has no limitation on types of data to be stored.

The controller 150 and the storage 160 may be implemented in separate chips, or incorporated in a single chip, without being limited thereto.

The medical imaging apparatus 100 may include a communicator 170.

The communicator 170 may include at least one of wired and wireless communication modules. The communicator 170 may then exchange data with an external device over at least one of wired and wireless communication networks. The wired communication module and the wireless communication module may be implemented in separate chips, or incorporated in a single chip, without being limited thereto.

In an embodiment, the communicator 170 may exchange data with a hospital server or another medical device in the hospital connected through a Picture Archiving and Communication System (PACS) over the wired and/or wireless communication network, according to a medical digital imaging and communications in medicine (DICOM) standard. In another embodiment, the communicator 170 may support sharing of data related to diagnosis of an object or medical images created by another medical imaging apparatus in a wired and/or wireless communication scheme, allowing a doctor to make an integrated diagnosis on the object.

In still another embodiment, the communicator 170 may receive information regarding the patient's diagnosis history or treatment schedule from a server, and use the information in the diagnosis of a subject. The communicator may also perform data communication not only with a server or medical equipment in the hospital but also with portable terminals of doctors or customers. In yet another embodiment, the communicator 170 may transmit information about whether the medical equipment has an error or information about quality of the medical image to the user over a wired and/or wireless communication network, and receive a feedback thereof from the user.

Meanwhile, at least one of the components of the medical imaging apparatus 100 may be included in the workstation 200. For example, referring to FIG. 7B, the user interface 130, the image processor 140, the controller 150, the storage 160, and the communicator 170 may be included in the workstation 200. The components of the medical imaging apparatus 100, which are not included in the workstation 200, such as the X-ray source 110, the X-ray detector 120, etc., are connected to the workstation 200 wiredly or wirelessly for exchanging various commands, data, etc.

Turning back to FIG. 1B, the workstation 200 may be equipped with the user interface 130 for user's manipulation. The user interface 130 may receive instructions or commands to control operation of the medical imaging apparatus 100 from the user, and provide various screens related to the operation of the medical imaging apparatus 100.

In an embodiment, the user interface 130 may be implemented with a display 131 for visually presenting various information for the user, a keyboard 132 for receiving various control commands from the user, and a mouse 133. The user interface 130 may also be implemented with a trackball, a foot switch, a foot pedal, or any device capable of performing interaction with the user without limitations. Furthermore, the user interface 130 may be arranged on top of the main body 200 as shown in FIG. 1B, or on the bottom if it is implemented with the foot switch and/or the foot pedal.

The user interface 130 may enable interaction between the user and the medical imaging apparatus 100 by displaying a Graphical User Interface (GUI) on the display 131, which implements operation of exchanging various information and commands between the user and the medical imaging apparatus 100 in graphics to facilitate the operation. In this case, the user interface 130 may be implemented only by the display 131.

The user interface 130 may receive control commands for operation of the medical imaging apparatus 100 from the user, such as commands for moving the table 190 with an object lying thereon, commands for selecting an X-ray scan mode, commands regarding X-ray scan conditions, commands for displaying scanned images, etc. Besides, the user interface 130 may allow the user to place a command to start an X-ray scan, a command to select a scan type, a command to set a region of interest, etc., without being limited thereto.

Meanwhile, the housing 101 including components for performing a scan on an object may be placed along with the workstation 200 in a scanning room. Alternatively, the scanning room where a scan of the object is performed, and a control room where scanning and image processing operations on the object are performed may be separated. The housing 101 including the components for performing a scan on an object may be placed in the scanning room while the workstation 200 may be placed in the control room.

However, the workstation 200 may not only be placed in the control room, in which case the scanning process to scan an object may be performed in the control room while the image processing may be performed in a separate room. In this regard, the workstation 200 performing the scanning process in the control room corresponds to a first workstation, and that performing the image processing process in the separate room corresponds to a second workstation. The workstation 200 may include at least one of the first and second workstations.

An operation flow of the medical imaging apparatus 100 will now be briefly described.

Figure 15:
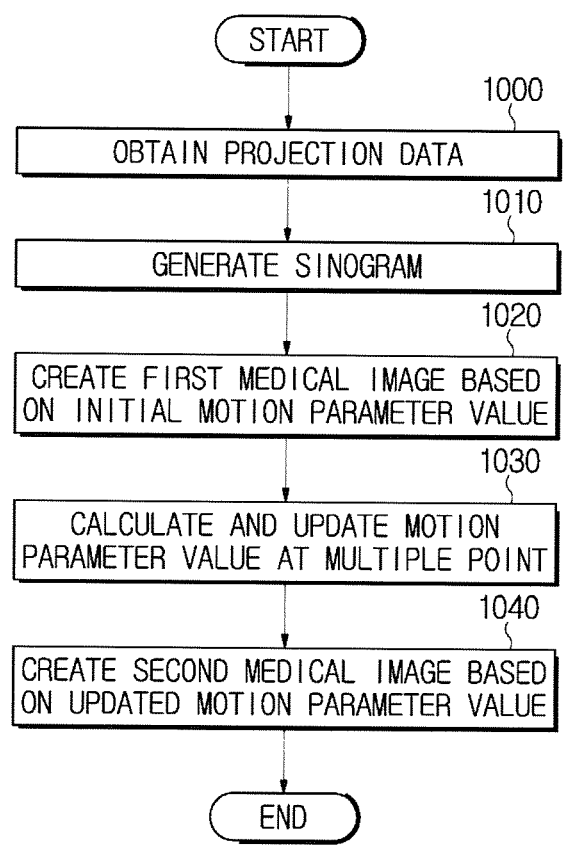
FIG. 15 illustrates a flowchart illustrating operation of a medical imaging apparatus for creating a second medical image based on motion parameter values, according to various embodiments of the present disclosure.

FIG. 15 is a flowchart illustrating operation of a medical imaging apparatus for creating a second medical image based on motion parameter values, according to an embodiment of the present disclosure.

Referring to FIG. 15, a medical imaging apparatus obtains raw data through an X-ray detector and obtains projection data by performing preprocessing on the raw data, as described above, in operation 1000. The projection data refers to data derived from the preprocessing process on the row data in all channels at a particular scan angle or scan point of time.

The medical imaging apparatus collects the projection data at all scan angles to create a sinogram, in operation 1010. The sinogram refers to a set of projection data at all scan angles.

Accordingly, the medical imaging apparatus creates a first medical image by applying a mathematical process, such as a weighting process and a filtering process on the sinogram, and applying a back projection process, in operation 1020. The first medical image is an image reconstructed based on preset initial motion parameter values without reflecting a motion the object has had during the scan.

The medical imaging apparatus may determine motion parameter values from the first medical image. For example, the motion parameter refers to a parameter for representing an extent of motion of a region of interest of the object. In the Cartesian coordinate system, the motion parameter may be represented by 6 values: distances that the object has been moved along the x-axis, the y-axis, and the z-axis, and respective moving directions from an origin, a position of the region of interest of the object at the start of the scan. The motion parameter may further include a value for representing a distance between the X-ray source and the X-ray detector.

During a scan, distances between the X-ray source, the X-ray detector, and the object may vary by the motion of the object itself or by the motion of a component of the medical imaging apparatus 100. For example, as described above, as in a mobile CT device, if a scan is performed while the X-ray source and X-ray detector are moved along the D1 axis of FIG. 5 or while the table is moved along the D1 axis, stability decreases and the distances between the X-ray source, the X-ray detector, and the object are more likely to vary. Accordingly, the medical imaging apparatus in an embodiment may determine motion parameter values including not only the motion of the object itself but also a relative motion of the object reflecting a motion of a component of the medical imaging apparatus.

For example, the medical imaging apparatus may use an image quality process, one of image quality estimation schemes, to calculate motion parameter values at particular points, and update the motion parameter values based on the calculation result. In this regard, the medical imaging apparatus may apply the image quality process by setting a variable to a motion parameter value and set at least one of a gradient value and a sharpness value with respect to an edge of an area that represents the object in the first medical image and an entropy value to a resultant value. The resultant value is also referred herein to as an image quality metric value.

In an embodiment, if the image quality metric value corresponds to at least one of the sharpness value and the gradient value, the medical imaging apparatus may update a motion parameter value of when the image quality metric value is maximized with the motion parameter value at the corresponding scan point of time or scan time. In another embodiment, if the image quality metric value corresponds to the entropy value, the medical imaging apparatus may update a motion parameter value of when the image quality metric value is minimized with the motion parameter value at the corresponding scan point of time or scan time.

Since the motion of the object is continuous, it may vary by every scan point of time or every scan time. In this case, obtaining the motion parameter value at every scan point of time or every scan time may cause overload of calculation. Accordingly, the medical imaging apparatus may update the motion parameter value by repeatedly performing the operation of determining the motion parameter value at several particular points, and calculate motion parameter values at the entire points based on the updating result. In this regard, a point may be set based on a scan point of time, i.e., a view or a scan time.

For example, the medical imaging apparatus may set a plurality of control points among scan points of time or scan time, determine motion parameter values at the plurality of control points, and form a graph by approximation of the motion parameter values at all the scan points of time of in the entire scan time based on the determined motion parameter values.

The medical imaging apparatus may form graphs for the respective motion parameters at all the scan points of time or in the entire scan time based on the motion parameter values at the plurality of control points, and update the motion parameter value at all the scan points of time or in the entire scan time.

Furthermore, the medical imaging apparatus creates a second medical image based on the updated motion parameter values, in operation 1040. The second medical image refers to a medical image reconstructed by compensating the motion of the object, i.e., a medical image reconstructed based on the updated motion parameters through the aforementioned process.

For example, the medical imaging apparatus may use the graphs for the respective motion parameters to generate a virtual trajectory of the X-ray source. The virtual trajectory of the X-ray source refers to a trajectory generated by compensating an actual trajectory along which the object has moved while the X-ray source is irradiating X-rays for the motion of the object. In other words, if the object has moved a particular distance in a particular direction from an origin at a particular point of time, the medical imaging apparatus may generate the virtual trajectory by compensating the X-ray source as if the X-ray source is moved the particular distance in the opposite direction of the particular direction.

For example, if the X-ray source has been moved a particular distance in a particular direction at a particular point of time, the motion parameter may represent that the object has moved the particular distance in the opposite direction of the particular direction. The medical imaging apparatus may then compensate for the motion of the object to generate a virtual trajectory on which the X-ray source has been moved the particular distance in the particular direction at the particular point of time, thereby even reflecting the motion of the X-ray source.

Accordingly, the medical imaging apparatus may reflect distances between the X-ray source, the object, and the X-ray detector based on the virtual trajectory in applying the weighting process, filtering process, and back projection process for the projection data. In addition, the medical imaging apparatus may provide the second medical image with intensity values of the object reconstructed more accurately, by setting a tangential direction to the virtual trajectory to a filtering direction in applying the filtering process.

Figure 16:
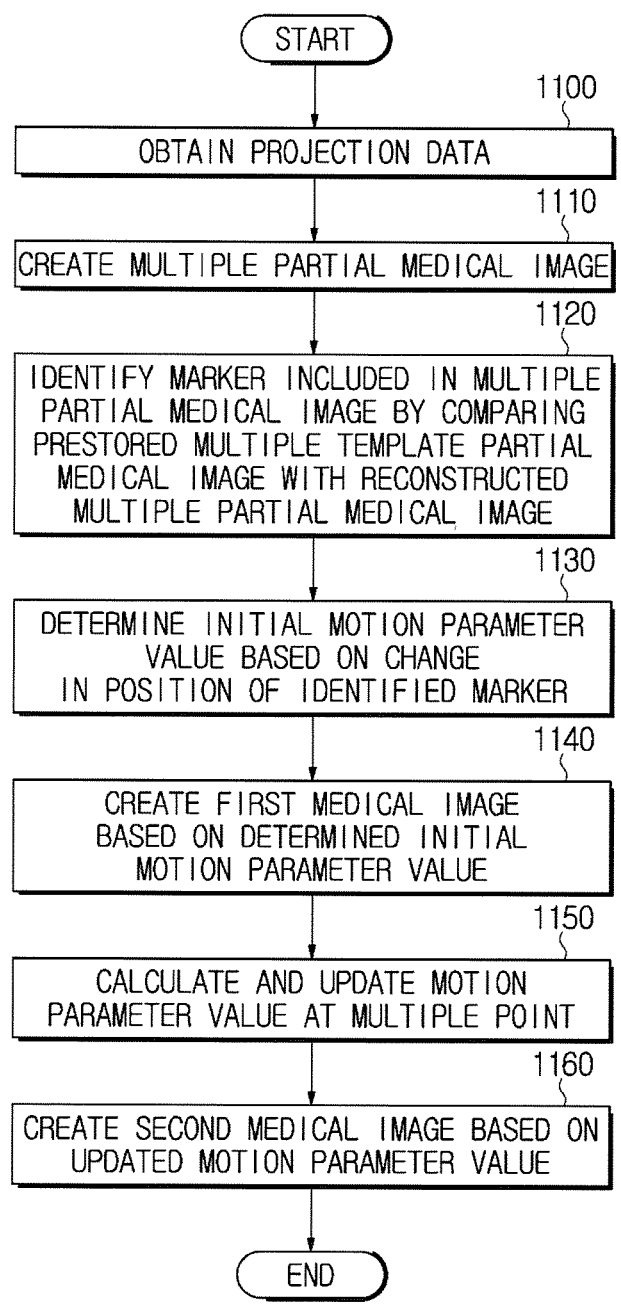
FIG. 16 illustrates a flowchart illustrating operation of a medical imaging apparatus for creating a second medical image based on initial motion parameter values determined using partial medical images, according to various embodiments of the present disclosure.

FIG. 16 is a flowchart illustrating operation of a medical imaging apparatus for creating a second medical image based on initial motion parameter values determined using a partial medical image, according to an embodiment of the present disclosure.

Referring to FIG. 6, a medical imaging apparatus obtains projection data, in operation 1100. How to obtain the projection data is the same as what is described in operation 1000, so the detailed description will be omitted. The medical imaging apparatus may generate a plurality of partial sinograms by dividing projection data at all scan angles or all scan points of time by a predetermined range of scan angles or of scan points of time. The partial sinogram refers to a set of projection data in the predetermined range of scan angles or of scan points of time.

The medical imaging apparatus creates a plurality of partial medical images by applying a mathematical process, such as a weighting process and a filtering process on the respective sinograms, and applying a back projection process, in operation 1110.

The medical imaging apparatus may identify a marker included in the created partial medical image by comparing a template partial medical image stored ahead of time and the created partial medical image. As a figure of the marker in a particular range of scan points of time or of scan angles is included in the stored template partial medical image, the medical imaging apparatus identifies the marker in the created partial medical image based on the figure of the marker included in the stored template partial medical image, in operation 1120.

The medical imaging apparatus determines initial motion parameter values based on changes in position of the marker in the plurality of partial medical images, in operation 1130. If the initial motion parameter values fail to reflect the motion of the object, a lot of calculation and time is required in determining correct motion parameter values. Accordingly, the medical imaging apparatus in an embodiment may roughly determine initial motion parameter values that reflect the motion of the object by tracking the position of the marker, and then calculate correct motion parameter values based on the determined initial motion parameter values to replace or update the initial motion parameter values with the correct motion parameter values.

For example, the medical imaging apparatus in an embodiment may set at least one reference point, and determine initial motion parameter values at the at least one reference point.

The reference point may be set in various ways. For example, in a case that 4 partial medical images are created by dividing the entire scan angle of 360° by four, the respective partial medical images may be reconstructed based on raw data obtained in the respective ranges of scan angle of 90°. In an embodiment, as described above, the first partial medical image may be reconstructed based on raw data obtained in a range of scan angle ranging from 0° to 90° (non-inclusive), the second partial medical image from 90° to 180° (non-inclusive), the third partial medical image from 180° to 270° (non-inclusive), and the fourth partial medical image from 270° to 360° (non-inclusive).

The reference point may be set based on 45° corresponding to an average of the range of scan angle of 90°. For example, the reference points in the first to fourth partial medical images are set to 45°, 135°, 225°, and 315°, respectively.

Besides, the medical imaging apparatus may set a plurality of reference points in various ways. As the more the number of the reference points, the higher the amount of calculation, the medical imaging apparatus may set the reference points as many as set in advance or determine a processable amount of calculation, and automatically set the reference point based on the determination, without being limited thereto.

The medical imaging apparatus determines initial motion parameter values at a reference point by tracking changing positions of the marker in the partial medical images, in operation 1130, and determines a graph of the initial motion parameter values by approximation.

The medical imaging apparatus creates a first medical image by applying a mathematical process, such as a weighting process and a filtering process on the entire sinograms, and applying a back projection process, in operation 1140. The first medical image may be an image reconstructed based on initial motion parameter values that reflect motions of the object with the marker.

The medical imaging apparatus may calculate motion parameter values from the first medical image. In this regard, since the first medical image reflects the motion of the object with the marker, the medical imaging apparatus calculates correct motion parameter values more promptly, and then updates motion parameter values with the calculated ones, in operation 1150.

The medical imaging apparatus may create a second medical image based on the updated motion parameter values, in operation 1160. The operation is the same as what is described in operation 1040, so the detailed description will be omitted.

If the object has a lot of motions, an amount of calculation and time required to create the second medical image may vary depending on how the initial motion parameter values are set. Accordingly, the medical imaging apparatus may calculate motion parameter values more promptly from the first medical image by creating a plurality of partial medical images, tracking the position of the marker in the plurality of partial medical images, and creating the first medical image that reflects the motion of the object. The medical imaging apparatus may then create the second medical image more promptly as well.

Figure 17:
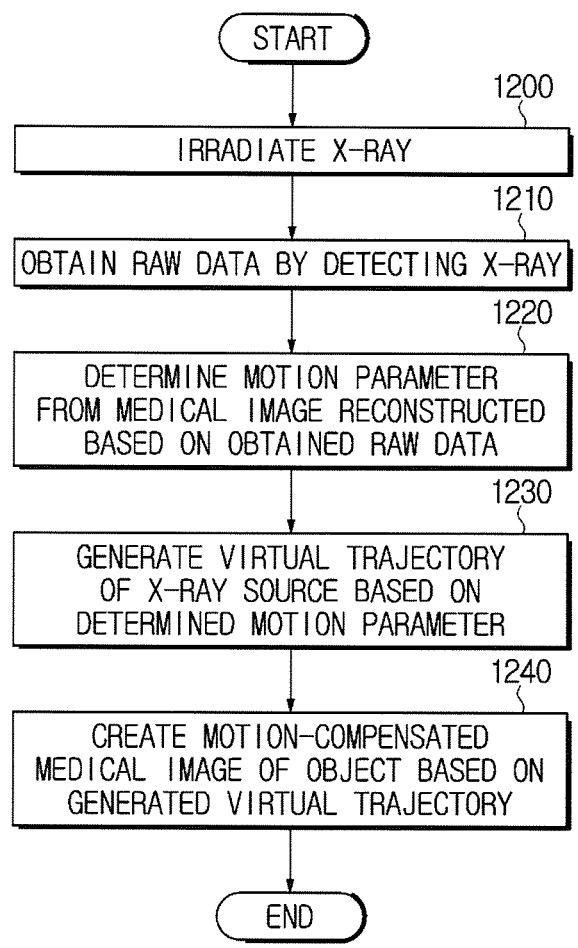
FIG. 17 illustrates a flowchart for an operation of a medical imaging apparatus for creating a motion-compensated medical image of an object by X-ray irradiation, according to various embodiments of the present disclosure.

FIG. 17 is a flowchart illustrating operation of a medical imaging apparatus for creating a medical image with compensation for a motion of an object by X-ray irradiation, according to an embodiment of the present disclosure.

Referring to FIG. 17, a medical imaging apparatus irradiates X-rays onto an object through an X-ray source, in operation 1200. The medical imaging apparatus may scan a region of interest of the object by irradiating X-rays while rotating the X-ray source 360° around the region of interest of the object to be diagnosed through a medical image.

Since an X-ray detector is located on the opposite side of the X-ray source, the medical imaging apparatus detects X-rays irradiated from the X-ray source and then penetrating inside or outside of the object through the X-ray detector, and obtains raw data by conversion of the detected X-rays, in operation 1210.

The medical imaging apparatus determines motion parameters from a medical image reconstructed based on the raw data, in operation 1120. The medical imaging apparatus may determine motion parameters from a medical image without need for an external device or camera for determining the motion of an object, by attaching an extra marker on the region of interest of the object and tracking the marker, and may create and provide a motion-compensated medical image based on the determined motion parameters. Accordingly, the medical imaging apparatus in the embodiments may reduce the expense as well as increase image quality of the medical image. Detailed description of how to determine the motion parameter from the medical image was described above.

The medical imaging apparatus generates a virtual trajectory of the X-ray source based on the determined motion parameters, in operation 1130. The object keeps moving and thus changing its position from its initial position over a scan time. An actual moving trajectory of the X-ray source is fixed. Accordingly, the medical imaging apparatus may generate a virtual trajectory of the X-ray source in a virtual space by reflecting the motion of the object. In reconstructing 3D medical images, the medical imaging apparatus may reflect distances between the X-ray source, the object, and the X-ray detector based on the virtual trajectory on a required operation process and reflect a tangential direction to the virtual trajectory as a filtering direction as described above. Accordingly, the medical imaging apparatus creates a motion-compensated medical image of the object, in operation 1140, and visually presents the created medical image for the user through a display.

Embodiments and features as described and illustrated in the present disclosure are only preferred examples, and various modifications thereof may also fall within the scope of the disclosure.

The terminology used herein is for the purpose of describing particular embodiments only and is not intended to limit the present disclosure. It is to be understood that the singular forms "a," "an," and "the" include plural references unless the context clearly dictates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The terms including ordinal numbers like "first" and "second" may be used to explain various components, but the components are not limited by the terms. The terms are only for the purpose of distinguishing a component from another. Thus, a first element, component, region, layer or section discussed below could be termed a second element, component, region, layer or section without departing from the teachings of the present disclosure. Descriptions shall be understood as to include any and all combinations of one or more of the associated listed items when the items are described by using the conjunctive term "~ and/or ~," or the like.

Furthermore, the terms as used throughout the specification, such as "~ part", "~ block", "~ member", "~ module", etc., may mean a unit of handling at least one function or operation. For example, it may refer to software or hardware, such as field programmable gate arrays (FPGAs) or application specific integrated circuits (ASICs). However, the terms "~ part", "~ block", "~ member", "~ module", etc., are not limited to software or hardware, but may be any element to be stored in an accessible storage medium and processed by one or more processors.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A medical imaging apparatus comprising:
   an X-ray source configured to irradiate X-rays;
   an X-ray detector configured to obtain raw data by detecting the X-rays irradiated from the X-ray source; and
   an image processor configured to compensate for a motion of an object relative to a motion of at least one of the X-ray source and the X-ray detector by:
      determining a motion parameter to represent motion of at least one of: the object, the X-ray source, or the X-ray detector from a medical image reconstructed based on the obtained raw data, and
      reconstructing a motion-compensated medical image of the object based on a virtual trajectory of the X-ray source generated based on the determined motion parameter.

2. The medical imaging apparatus of claim 1, wherein the image processor is further configured to determine a motion parameter value at at least one scan point of time or scan time by applying an image quality metric process on the medical image reconstructed based on the obtained raw data.

3. The medical imaging apparatus of claim 2, wherein the image processor is further configured to:
   set at least one control point,
   determine a motion parameter value at the at least one control point, and
   form a graph for each motion parameter by approximation of the determined motion parameter value.

4. The medical imaging apparatus of claim 2, wherein the image processor is further configured to:
   set the motion parameter to be a variable,
   apply the image quality metric process in which at least one of an entropy value, a sharpness value, and a gradient value is set to be a resultant value, and
   determine a motion parameter value at at least one scan point of time or scan time.

5. The medical imaging apparatus of claim 3, wherein the image processor is further configured to:
   calculate a motion parameter value at each scan point of time or scan time using the graph, and
   generate a virtual trajectory of the X-ray source by reflecting motion of the object based on the calculated motion parameter value.

6. The medical imaging apparatus of claim 1, wherein the image processor is further configured to perform a weighting process on projection data derived from the raw data based on a distance between the X-ray source and the X-ray detector on the virtual trajectory of the X-ray source.

7. The medical imaging apparatus of claim 1, wherein the image processor is further configured to perform a filtering process on projection data derived from the raw data based on a tangential direction of the virtual trajectory of the X-ray source.

8. The medical imaging apparatus of claim 1, wherein the motion parameter comprises a parameter to represent a distance between the X-ray source and the X-ray detector.

9. The medical imaging apparatus of claim 1, wherein the image processor is further configured to identify a marker in a partial medical image obtained by irradiation of X-rays on the object with a marker attached thereon by comparing a pre-stored template partial medical image with the partial medical image.

10. The medical imaging apparatus of claim 9, wherein the image processor is further configured to:
determine an initial motion parameter value by tracking a position of the marker identified in a partial medical image, and
reconstruct a motion-compensated medical image of the object based on the determined initial motion parameter value.

11. A workstation comprising:
an interface configured to receive a command to scan an object from a user;
a controller configured to control operation of an X-ray source and X-ray detector to obtain raw data under the received command; and
an image processor configured to compensate for a motion of the object relative to a motion of at least one of the X-ray source and the X-ray detector by:
create a first medical image from the raw data,
generate a virtual trajectory of the X-ray source based on a motion parameter determined from the first medical image, and
reconstruct a motion-compensated second medical image of the object based on the virtual trajectory of the X-ray source.

12. The workstation of claim 11, wherein the image processor is further configured to perform a weighting process on projection data derived from the raw data based on one of the determined motion parameters that represents a distance between the X-ray source and the X-ray detector.

13. The workstation of claim 11, wherein the image processor is further configured to determine a motion parameter value at at least one scan point of time or scan time by applying an image quality metric process on the first medical image reconstructed based on the obtained raw data.

14. The workstation of claim 11, wherein the image processor is further configured to perform a weighting process on projection data derived from the raw data based on a distance between the X-ray source and the X-ray detector on the virtual trajectory of the X-ray source.

15. A method for compensating for a motion of an object relative to a motion of at least one of an X-ray source and an X-ray detector, the method comprising:
receiving a command to scan an object from a user;
controlling operation of the X-ray source and the X-ray detector to obtain raw data under the received command;
creating a first medical image from the raw data;
generating a virtual trajectory of the X-ray source based on a motion parameter determined from the first medical image; and
reconstructing a motion-compensated second medical image of the object based on the virtual trajectory of the X-ray source.

16. The method of claim 15, further comprising performing a weighting process on projection data derived from the raw data based on a distance between the X-ray source and the X-ray detector on the virtual trajectory of the X-ray source.

17. The method of claim 15, wherein reconstructing a motion-compensated second medical image comprises determining a motion parameter value at least one scan point of time or scan time by applying an image quality metric process on the first medical image reconstructed based on the obtained raw data.

18. The method of claim 17, wherein reconstructing a motion-compensated second medical image comprises:
setting at least one control point,
determining a motion parameter value at the at least one control point, and
forming a graph for each motion parameter by approximation of the determined motion parameter value.

19. The method of claim 18, wherein restoring a background region of the first medical image based on a comparison of the first medical image and the motion-compensated second medical images comprises:
calculating a motion parameter value at each scan point of time or scan time using the graph, and
generating a virtual trajectory of the X-ray source by reflecting motion of the object based on the calculated motion parameter value.

* * * * *